(12) United States Patent
Mizukura et al.

(10) Patent No.: US 11,272,844 B2
(45) Date of Patent: Mar. 15, 2022

(54) INFORMATION PROCESSING DEVICE, INFORMATION PROCESSING METHOD, AND FLUORESCENCE IMAGE CAPTURING SYSTEM

(71) Applicant: Sony Corporation, Tokyo (JP)

(72) Inventors: Takami Mizukura, Kanagawa (JP); Minori Takahashi, Kanagawa (JP); Kenji Takahashi, Kanagawa (JP); Kentaro Fukazawa, Tokyo (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/761,800

(22) PCT Filed: Oct. 18, 2018

(86) PCT No.: PCT/JP2018/038755
§ 371 (c)(1),
(2) Date: May 6, 2020

(87) PCT Pub. No.: WO2019/093089
PCT Pub. Date: May 16, 2019

(65) Prior Publication Data
US 2021/0177263 A1    Jun. 17, 2021

(30) Foreign Application Priority Data
Nov. 13, 2017 (JP) .............................. JP2017-218188

(51) Int. Cl.
*A61B 5/00* (2006.01)
*G06F 3/14* (2006.01)
(Continued)

(52) U.S. Cl.
CPC .......... *A61B 5/0071* (2013.01); *G06T 7/0012* (2013.01); *H04N 5/2256* (2013.01);
(Continued)

(58) Field of Classification Search
None
See application file for complete search history.

(56) References Cited

U.S. PATENT DOCUMENTS

2016/0022225 A1*  1/2016  Palmer ............. A61B 5/150358
                                                            600/367
2018/0082411 A1*  3/2018  Sato .................... G01N 21/6456
(Continued)

FOREIGN PATENT DOCUMENTS

JP    2006-280542 A    10/2006
JP    2007-330331 A    12/2007
(Continued)

OTHER PUBLICATIONS

International Search Report and Written Opinion dated Dec. 25, 2018 for PCT/JP2018/038755 filed on Oct. 18, 2018, 8 pages including English Translation of the International Search Report.

*Primary Examiner* — Patricia I Young
(74) *Attorney, Agent, or Firm* — Xsensus LLP

(57) ABSTRACT

[Problem] To predict a remaining time during which a fluorescence image is observable.
[Solution] An information processing device according to the present disclosure includes a remaining time estimation unit that estimates, on the basis of a luminance limit value for observation of a fluorescence image and a change in luminance of a fluorescence image, a remaining time until the luminance of the fluorescence image reaches the luminance limit value. This configuration enables the time at which the luminance of a fluorescence image reaches the luminance limit value to be estimated according to a change in luminance of the fluorescence image, and it is possible to predict a remaining time during which a fluorescence image is observable.

18 Claims, 16 Drawing Sheets

(51) Int. Cl.
*H04N 5/225* (2006.01)
*G06T 7/00* (2017.01)

(52) U.S. Cl.
CPC ....... *A61B 5/742* (2013.01); *A61B 2562/0242* (2013.01); *G06F 3/14* (2013.01); *G06T 2207/10024* (2013.01); *G06T 2207/10064* (2013.01); *G06T 2207/20104* (2013.01); *G06T 2207/20212* (2013.01)

(56) References Cited

U.S. PATENT DOCUMENTS

2019/0051022 A1* 2/2019 Kikuchi ................ G06T 11/001
2019/0376892 A1* 12/2019 Ishikawa ................ G01N 21/64

FOREIGN PATENT DOCUMENTS

| JP | 2008-070259 A | 3/2008 |
|----|---------------|--------|
| JP | 2014-023628 A | 2/2014 |
| JP | 2014-025774 A | 2/2014 |
| JP | 2015-029841 A | 2/2015 |
| JP | 2016-202708 A | 12/2016 |
| WO | 2014/137989 A1 | 9/2014 |
| WO | 2017/073302 A1 | 5/2017 |

* cited by examiner

FIG.2
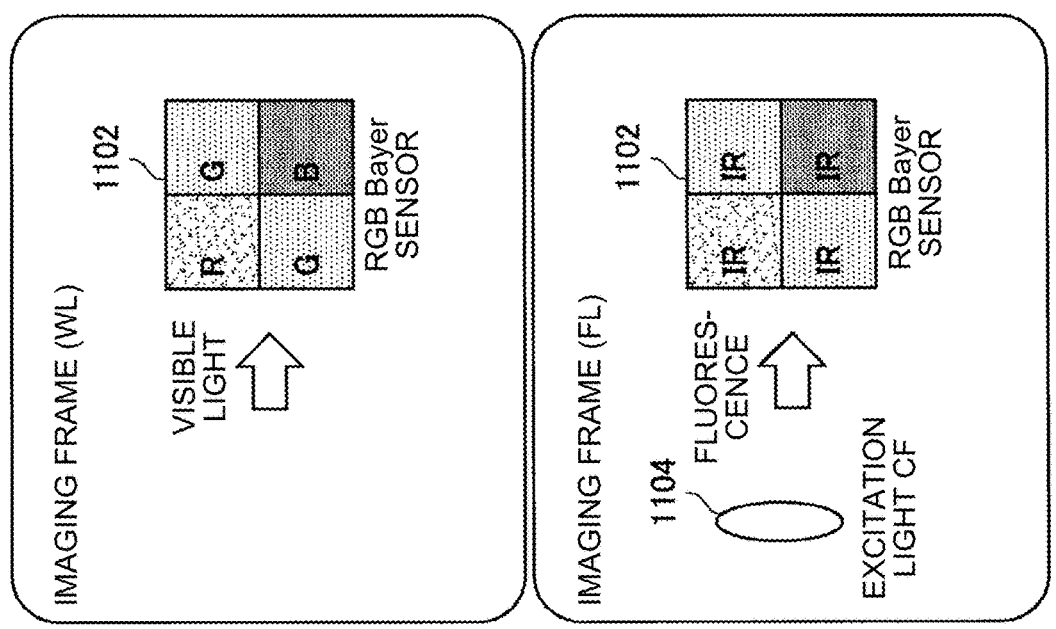
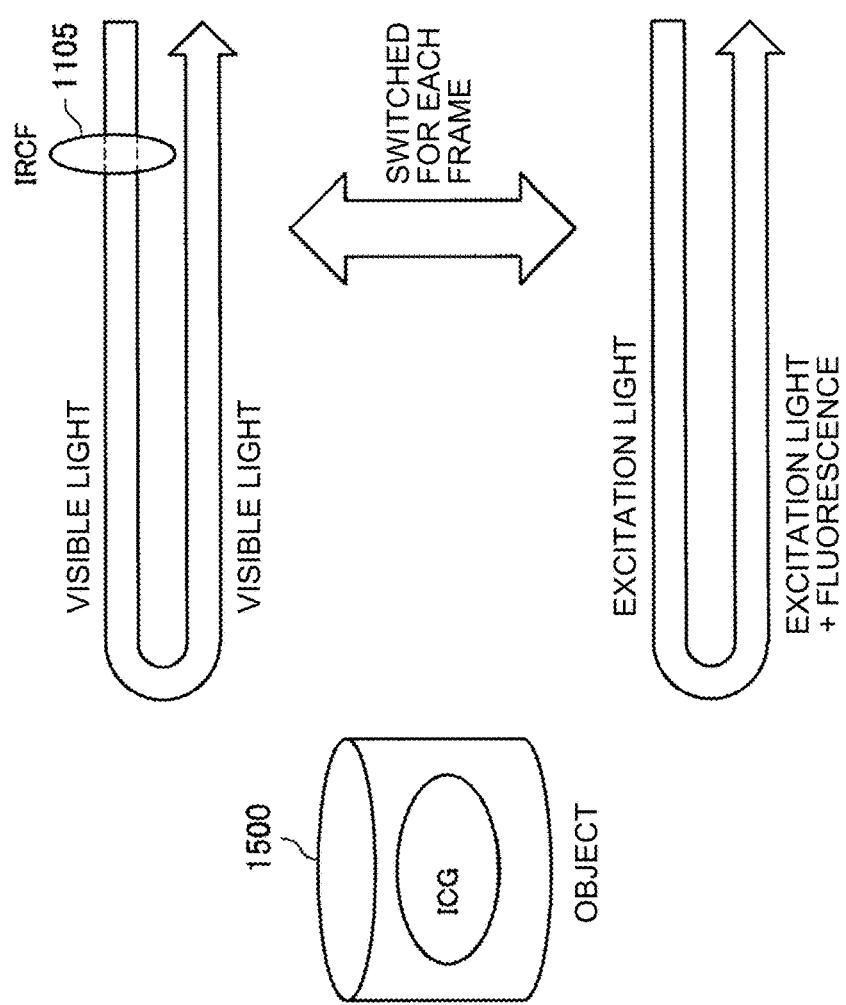

DISPLAYED IN BAR FORM

ALTERNATELY BLINKED WHEN
ESTIMATED REMAINING TIME IS REDUCED

CHANGE COLOR ACCORDING TO TIME

INFORMATION PROCESSING DEVICE, INFORMATION PROCESSING METHOD, AND FLUORESCENCE IMAGE CAPTURING SYSTEM

CROSS-REFERENCE TO RELATED APPLICATIONS

The present application is based on PCT filing PCT/JP2018/038755, filed Oct. 18, 2018, which claims priority to JP 2017-218188, filed Nov. 13, 2017, the entire contents of each are incorporated herein by reference.

FIELD

The present disclosure relates to an information processing device, an information processing method, and a fluorescence image capturing system.

BACKGROUND

For example, Patent Literature 1 described below discloses a conventional imaging device imaging a plurality of wavelength bands, in which the imaging device includes a first imaging unit that captures a light image in a near-infrared light band, a second imaging unit that captures a light image in a visible light band, an image processing unit that performs necessary information extraction processing on a near-infrared image acquired by the first imaging unit, and a composite image generation unit that adds a visible light image acquired by the second imaging unit to an image obtained by the image processing unit, in a predetermined ratio, and generates a composite image.

CITATION LIST

Patent Literature

Patent Literature 1: JP 2015-029841 A

SUMMARY

Technical Problem

Surgery performed using an endoscope, microscope, or the like is usually performed while observing an image (hereinafter, also referred to as a visible light image) obtained by emitting broadband light of visible light from xenon (Xe), white LED, or the like. However, in the visible light image, important blood vessels, lymph vessels/nodes, bile ducts, and the like hidden by epithelial tissue and fat cannot be seen, and a problem arises that the presence or absence of blood flow or lymph flow cannot be recognized, a lesion cannot be identified, or the like.

Therefore, a fluorescent agent (ICG, Laserphyrin, 5ALA, etc.), which has high safety to a living body, is injected into tissue to be observed or fluorescence stain, such as fluorescence in-situ hybridization (FISH) or enzyme antibody technique, is performed on the tissue of the living body to observe a fluorescence image obtained by imaging fluorescence emission from the agent irradiated with excitation light. This makes it possible to understand the tissue and state of the living body, which are difficult to confirm in the visible light image. Furthermore, in recent years, instead of observation of only the fluorescence image alone, observation of two images of a fluorescence image and a visible image, which are acquired simultaneously and superimposed on each other, has been aggressively performed to advance surgery more safely.

However, there is a problem that fluorescent observation is allowed only in a limited time period due to a limited time of fluorescence emission. Furthermore, when a fluorescence image and a visible light image are superimposed on each other, different superimposition rates bring about different observation degrees, and it becomes difficult to adjust the images to an easily observable state or to predict an observable time. The unpredictable observable time may give anxiety and stress to a doctor, triggering a surgical accident. Furthermore, a fluorescent agent is sometimes injected again to increase the intensity of fluorescence which weakens, but if the injection is performed on the basis of sensuous judgment, the injection may lead to excessive injection of the agent into a human body, increasing invasiveness.

Therefore, it has been desired to predict a remaining time during which a fluorescence image is observable.

Solution to Problem

According to the present disclosure, an information processing device is provided that includes a remaining time estimation unit that estimates, on the basis of a luminance limit value for observation of a fluorescence image and a change in luminance of a fluorescence image, a remaining time until the luminance of the fluorescence image reaches the luminance limit value.

Moreover, according to the present disclosure, an information processing method is provided that includes estimating, on the basis of a luminance limit value for observation of a fluorescence image and a change in luminance of a fluorescence image, a remaining time until the luminance of the fluorescence image reaches the luminance limit value.

Moreover, according to the present disclosure, a fluorescence image capturing system is provided that includes: an imaging device that captures a fluorescence image; a light source that emits light to an object imaged by the imaging device; and an information processing device including a remaining time estimation unit that estimates, on the basis of a luminance limit value for observation of a fluorescence image and a change in luminance of a fluorescence image, a remaining time until the luminance of the fluorescence image reaches the luminance limit value.

Advantageous Effects of Invention

As described above, according to the present disclosure, it is possible to predict the remaining time during which a fluorescence image is observable.

Note that the effects described above are not necessarily limitative, and with or in place of the above effects, there may be achieved any one of the effects described in this description or other effects that may be grasped from this description.

BRIEF DESCRIPTION OF DRAWINGS

FIG. 2 is a schematic diagram illustrating a frame sequential (FS) system.

DESCRIPTION OF EMBODIMENTS

Figure 1:
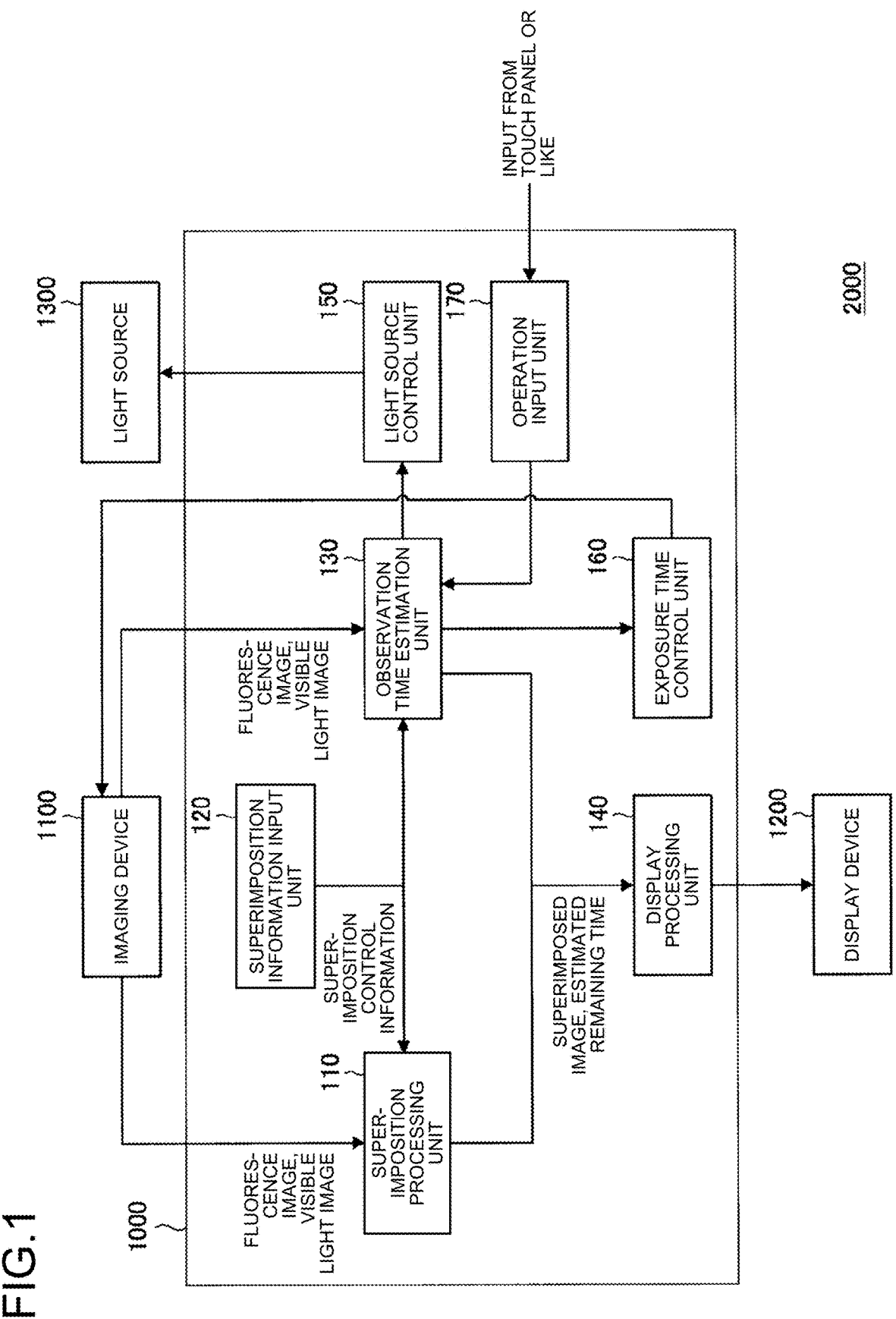
FIG. 1 is a schematic diagram illustrating a configuration of a system according to an embodiment of the present disclosure.

Hereinafter, preferred embodiments of the present disclosure will be described in detail with reference to the accompanying drawings. Note that, in this description and the drawings, component elements having substantially the same functional configurations are denoted by the same reference numerals and repeated description thereof is omitted.

Note that a description will be made in the following order.

1. Overview of system
2. Configuration of imaging device
3. Configuration of superimposition processing unit
4. Configuration of observation time estimation unit
5. Configuration of display processing unit
6. About extension of remaining observation time 1. Overview of System FIG. 1 is a schematic diagram illustrating a configuration of a system 2000 according to an embodiment of the present disclosure. As illustrated in FIG. 1, the system 2000 includes an image processing device (information processing device) 1000, an imaging device 1100, a display device 1200, and a light source 1300.

The image processing device 1000 includes a superimposition processing unit 110, a superimposition information input unit 120, an observation time estimation unit 130, a display processing unit 140, a light source control unit 150, an exposure time control unit 160, and an operation input unit 170.

The imaging device 1100 captures a fluorescence image and a visible light image simultaneously. A fluorescence image signal (hereinafter, referred to as fluorescence image) and a visible light image signal (hereinafter, referred to as visible light image) obtained by image capturing by the imaging device 1100 are input to the superimposition processing unit 110 and the observation time estimation unit 130. To the superimposition information input unit 120, a superimposition parameter (superimposition control information) for controlling a superimposition method is input by a user. The superimposition control information is input to the superimposition processing unit 110 and the observation time estimation unit 130.

In the superimposition processing unit 110, a fluorescence image and a visible light image are superimposed on each other according to a given superimposition control information and a superimposed image signal (hereinafter, referred to as superimposed image) is generated. The observation time estimation unit 130 estimates an observable time according to the decay of fluorescence emission. The display processing unit 140 performs processing for displaying a superimposed image, an observable time, or the like on the display device 1200.

The display device 1200 includes a liquid crystal display (LCD) or the like and displays on a display screen a superimposed image, an observable time, and other information, which are processed by the display processing unit 140, and makes a presentation to the user. The light source 1300 emits light to an object to be imaged by the imaging device 1100. The light source 1300 can include a visible light emission unit that emits visible light to an object, and an excitation light emission unit that emits excitation light for fluorescence to the object.

2. Configuration of Imaging Device

The imaging device 1100 includes an imaging element (imaging sensor) 1102. The imaging device 1100 can have a different configuration depending on method of capturing a fluorescence image and a visible light image. Here, three examples illustrated in FIGS. 2 to 4 will be given as the imaging device 1100. In each of the examples, the object 1500 is a living body, and indocyanine green (ICG) is injected as a fluorescent dye into the object 1500.

FIG. 2 is a schematic diagram illustrating a frame sequential (FS) system. In the frame sequential system, imaging is performed by switching emission of visible light and excitation light for fluorescence in a time division manner for each frame. A filter 1104 for cutting excitation light is mounted on a front surface of the imaging device 1100, and excitation light is not applied to the imaging element 1102 upon emission of excitation light. Therefore, only fluorescence is detected by the imaging element 1102, and a fluorescence image is obtained. On the other hand, when visible light is emitted, the filter 1104 is removed from the front surface of the imaging device 1100, and a visible light image is acquired by the imaging element 1102. The frame sequential system is a system that enables a fluorescence image and a visible light image to be captured alternately for each frame.

Figure 3:
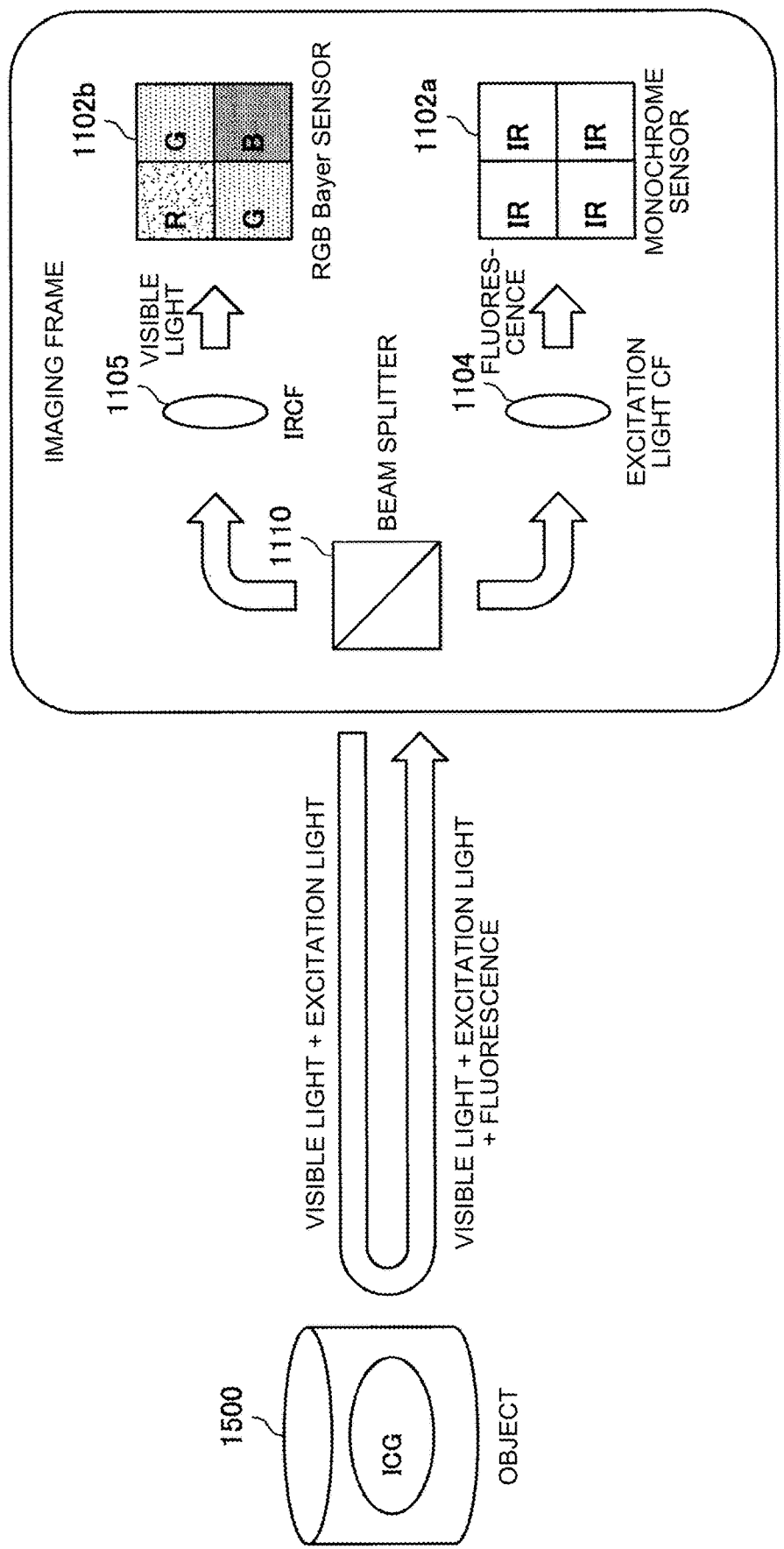
FIG. 3 is a schematic diagram illustrating a 2-CCD system.

FIG. 3 is a schematic diagram illustrating a 2-CCD system. In the 2-CCD system, an optical element 1110 such as a beam splitter or a dichroic mirror is provided closer to the object 1500 relative to imaging elements 1102*a* and 1102*b*. A mixture of visible light and excitation light is emitted to the object 1500, and reflected light of a specific wavelength is split by the optical element 1110. Two imaging elements, that is, the imaging element 1102*a* for detecting light containing excitation light and the imaging element 1102*b* for detecting light containing visible light, are prepared to detect respective light, and thus a fluorescence image and a visible light image can be obtained simultaneously. The filter 1104 cutting excitation light is provided in front of a sensor (imaging element 1102*a*) detecting fluorescence to prevent emission of the excitation light to the imaging element 1102*a* used to acquire fluorescence. In addition, in front of the imaging element 1102*b* for detecting visible light, a filter 1105 cutting infrared (IR) light is provided. In FIG. 3, the imaging element 1102*a* detecting fluorescence is described as a monochrome sensor, but any sensor may be used as long as the sensor has a sensitivity to fluorescence.

Figure 4:
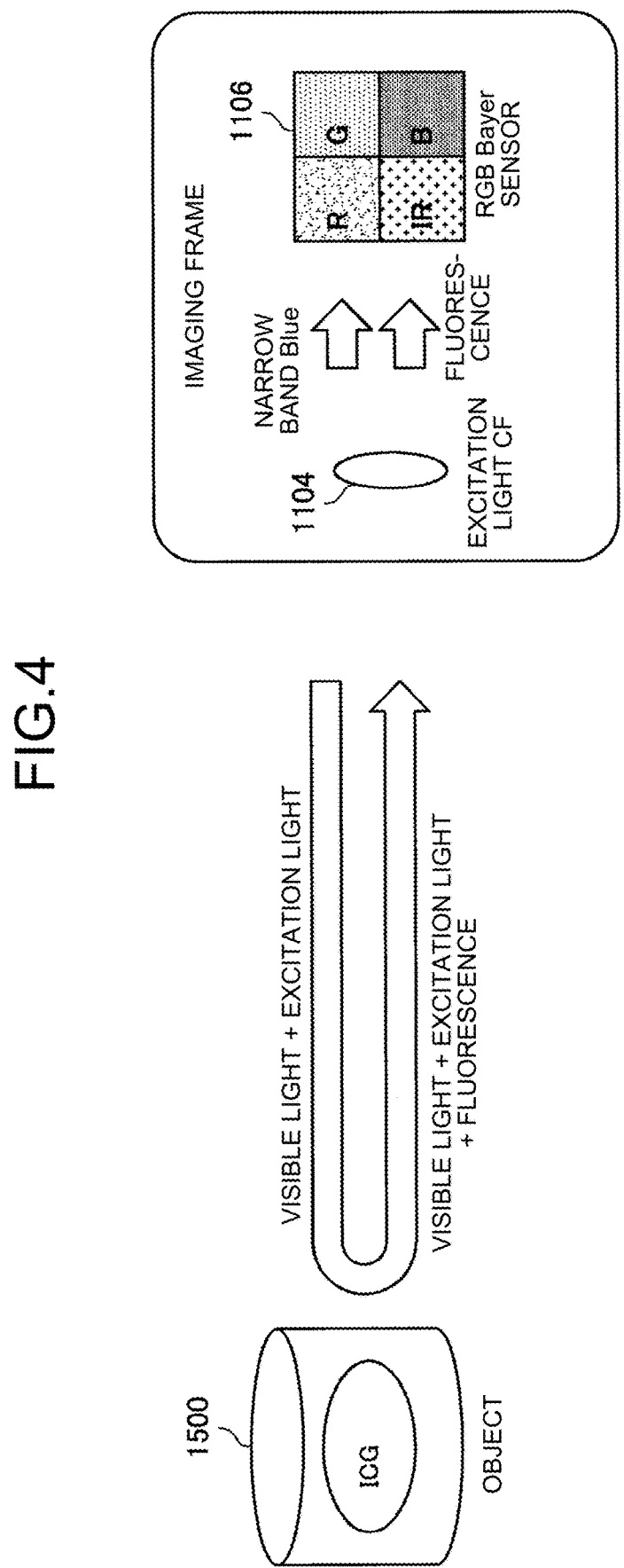
FIG. 4 is a schematic diagram illustrating a sensor system.

FIG. 4 is a schematic diagram illustrating a sensor system. An imaging element 1106 is provided that changes color filters to have an IR pixel sensitive only to IR wavelength band and an R pixel, G pixel, and B pixel sensitive to R, G, and B. A mixture of visible light and excitation light is emitted to the object 1500, and only excitation light returned as reflected light is cut by the filter 1104 or the like cutting the excitation light. Thus, a visible light image can be obtained with the R, G, and B pixels, and at the same time, a fluorescence image can be obtained with the IR pixel.

Note that the configuration of the imaging device 1100 is not limited to the above three examples, and any method may be used as long as the method enables a fluorescence image and a visible light image to be acquired with a certain simultaneity.

3. Configuration of Superimposition Processing Unit

The superimposition processing unit 110 superimposes a fluorescence image and a visible light image on the basis of a superimposition parameter to generate a superimposed image. A superimposition rate upon superimposing the fluorescence image and the visible light image may be uniform over the entire screen or may be changed spatially on the screen. Note that in the following, the superimposition rate of visible light (visible-light superimposition rate) upon superimposing a fluorescence image and a visible light image on each other is also referred to as α-blending ratio. Furthermore, the superimposition of the fluorescence image and the visible light image is also referred to as α-blending.

Figure 5:
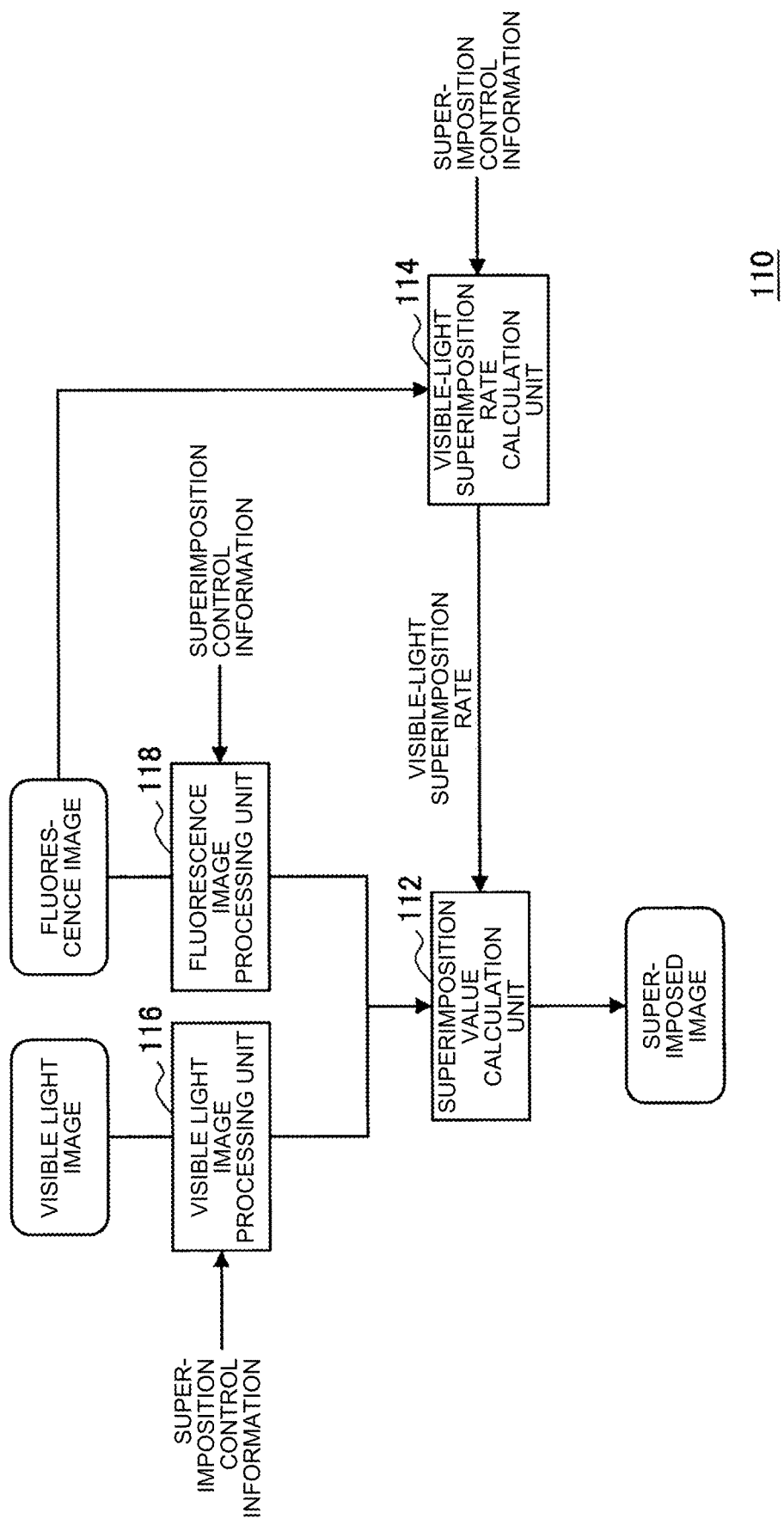
FIG. 5 is a schematic diagram illustrating a procedure in a superimposition processing unit.

Hereinafter, an example will be described in which the superimposition processing unit 110 creates a superimposed image by spatially changing the α-blending ratio between a portion where fluorescence is present and a portion where no fluorescence is present. FIG. 5 is a schematic diagram illustrating a procedure in the superimposition processing unit 110.

As illustrated in FIG. 5, the superimposition processing unit 110 includes a superimposition value calculation unit 112 and a visible-light superimposition rate calculation unit 114. The visible-light superimposition rate calculation unit 114 calculates a visible-light superimposition rate for each pixel. The superimposition processing unit 110 uses the visible-light superimposition rate to α-blend a visible light image and a fluorescence image for each pixel.

Furthermore, the superimposition processing unit 110 includes a visible light image processing unit 116 that performs image processing on a visible light image before superimposing the visible light image and a fluorescence image, and a fluorescence image processing unit 118 that performs processing on a fluorescence image before superimposing a visible light image and the fluorescence image.

(Visible-Light Superimposition Rate Calculation Unit)

The visible-light superimposition rate calculation unit 114 outputs the visible-light superimposition rate in response to input of a fluorescence image and superimposition control information. The fluorescence image is an image having a digital value corresponding to fluorescence intensity (luminance) and is usually a single channel monochrome image. In this case, a pixel value of a certain pixel is defined as (X). When the fluorescence image has a monochrome color, a color map is sometimes assigned according to fluorescence intensity, and in such a case the fluorescence image may be a color image. In this case, the fluorescence image often has pixel values representing three channels, and a color space can be variously defined by RGB, YCbCr, YIQ, L*a*b* (CIELAB), L*u*v*(CIELUV), or the like.

From such a fluorescence image, a fluorescence intensity value Yfl is defined. Yfl may have any value as long as the value has a correlation with fluorescence intensity and specifically corresponds to a luminance value or the like. When the fluorescence image is a single channel monochrome image, Yfl represents the pixel value (=X) itself, and when the fluorescence image is a color image, a channel corresponding to luminance may be defined as Yfl or Yfl may be defined by mixing luminance from three channel signals at an appropriate ratio.

Figure 6:
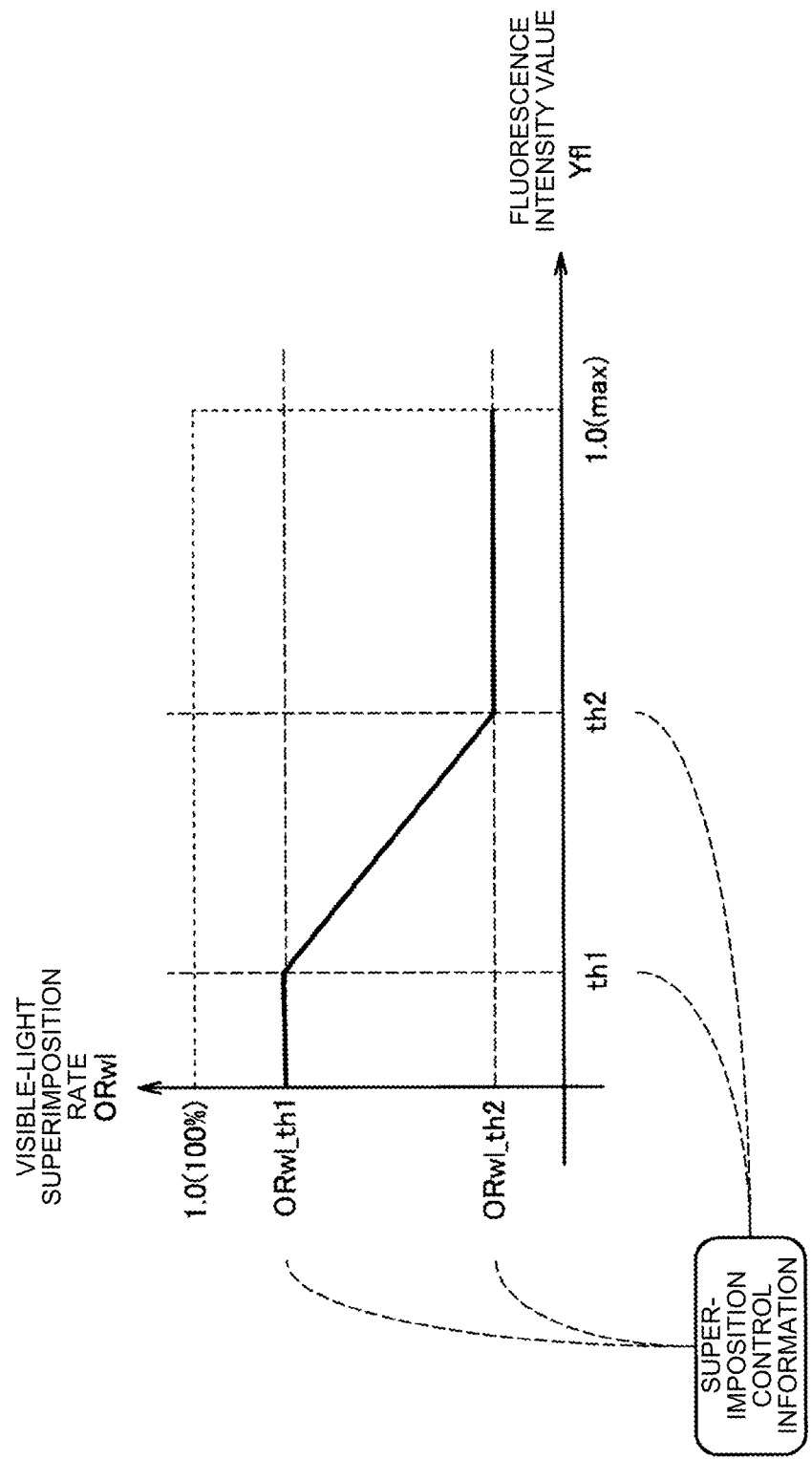
FIG. 6 is a schematic diagram illustrating a superimposition rate defining function for calculating a visible-light superimposition rate.

The visible-light superimposition rate is calculated on the basis of Yfl. FIG. 6 is a schematic diagram illustrating a superimposition rate defining function for calculating a visible-light superimposition rate. A visible-light superimposition rate ORwl can be calculated, for example, according to the superimposition rate defining function as illustrated in FIG. 6. This function is defined to increase the visible-light superimposition rate when the fluorescence intensity is low and to reduce the visible-light superimposition rate when the fluorescence intensity is high. A portion in Yfl where the intensity transitions is defined so that the superimposition rate also transitions gradually.

In the example illustrated in FIG. 6, the shape of the function is controlled by four parameters (th1, th2, ORwl_th1, ORwl_th2). These four parameters can be subjectively determined by the user and correspond to the superimposition control information described above. Note that the superimposition rate defining function illustrated in FIG. 6 can be defined as follows.

When $Yfl < th1$ $ORwl = ORwl\_th1;$

When $th1 \leq Yfl < th2$ $$a = \frac{ORwl\_th2 - ORwl\_th1}{th2 - th1}, b = ORwl\_th1 - a \times th1$$

$ORwl = a \times Yfl + b;$ $Yfl \geq th2$ $ORwl = ORwl\_th2;$

Although the function illustrated in FIG. 6 has a polygonal line shape, the function may be defined by a curve such as an S-shaped curve so as to smooth the transition. Furthermore, an appropriate type of superimposition control information may be prepared according to the curve.

(Superimposition Value Calculation Unit)

The superimposition value calculation unit 112 α-blends a visible light image and a fluorescence image according to the visible-light superimposition rate ORwl calculated by the visible-light superimposition rate calculation unit 114. Since different pixel values have different visible-light superimposition rates ORwl, different α-blending is performed for each pixel. As an example, a calculation formula for α-blending used when the visible light image is a color image defined in a YCbCr space is shown below.

$$Y_{ov} = ORwl \times Y_{wl} + (1.0 - ORwl) \times Y_{fl}$$

$$Cb_{ov} = ORwl \times Cb_{wl} + (1.0 - ORwl) \times Cb_{fl}$$

$$Cr_{ov} = ORwl \times Cr_{wl} + (1.0 - ORwl) \times Cr_{fl}$$

Furthermore, a calculation formula for α-blending used when the visible light image is a color image defined in an RGB space is shown below.

$$R_{ov} = OR\_wl \times R_{wl} + (1.0 - OR_{wl}) \times R_{fl}$$

$$G_{ov} = OR\_wl \times G_{wl} + (1.0 - OR_{wl}) \times G_{fl}$$

$$B_{ov} = OR\_wl \times B_{wl} + (1.0 - OR_{wl}) \times B_{fl}$$

In the YCbCr space, the pixel values of the visible light image are ($Y_{wl}$, $Cb_{wl}$, $Cr_{wl}$), and the pixel values of the fluorescence image are ($Y_{fl}$, $Cb_{fl}$, $Cr_{fl}$). When the fluorescence image has a single channel, it is assumed that the values of $Cb_{fl}$ and $Cr_{fl}$ are 0.

In the RGB space, the pixel values of the visible light image are ($R_{wl}$, $G_{wl}$, $B_{wl}$), and the pixel values of the fluorescence image are ($R_{fl}$, $G_{fl}$, $B_{fl}$). When the fluorescence image has a single channel, it is assumed that all RGB pixel values of the fluorescence image have the same value. In other words, in this case, $R_{fl} = G_{fl} = B_{fl} = Y_{fl}$.

Since the visible-light superimposition rate is ORwl, the superimposition rate of fluorescence has a value obtained by subtracting ORwl from 100%, that is, 1.0−ORwl. When the respective superimposition rates are multiplied by corresponding pixel values and then the multiplied values are added together, the pixel values ($Y_{ov}$, $Cb_{ov}$, $Cr_{ov}$) or ($R_{ov}$, $G_{ov}$, $B_{ov}$) of the superimposed image are obtained.

Figure 8:
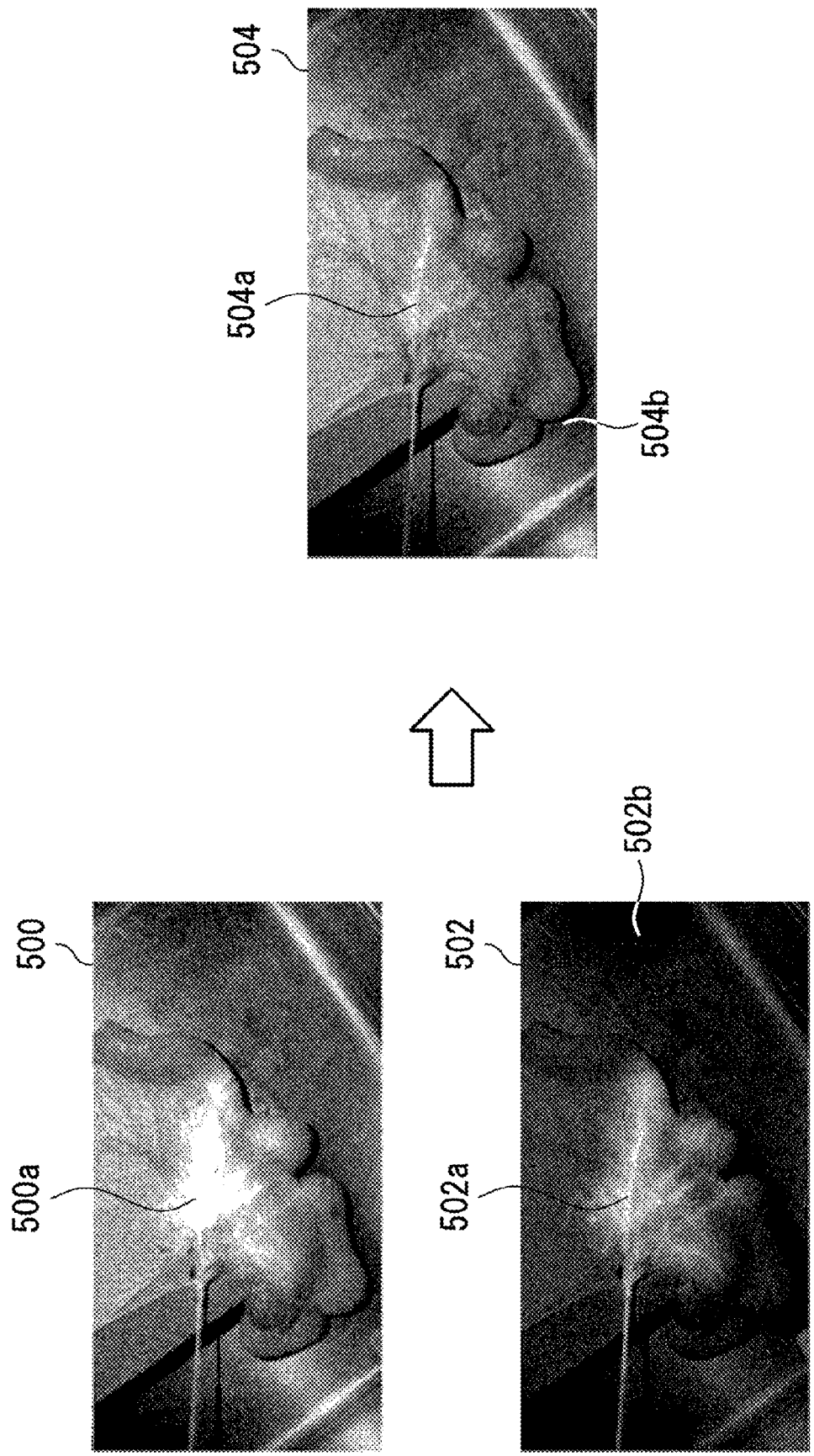
FIG. 8 is a schematic diagram illustrating an example of a superimposed image.

FIG. 8 is a schematic diagram illustrating an example of a superimposed image. An image 500 illustrated in FIG. 8 shows that a fluorescence image and a visible light image are simply superimposed. In this case, a fluorescence region 500*a* is partially saturated, which may obstruct observation. Furthermore, as shown in an image 502, if a wrong superimposition rate is applied, a background region 502*b* around a fluorescence portion 502*a* becomes dark, which may also obstruct observation.

On the other hand, an image 504 illustrated in FIG. 8 shows a superimposed image generated by a method according to the present embodiment. As shown in the image 504, according to the method of the present embodiment, a background region 504*b* becomes bright as well as a fluorescent region 504*a*, and both regions are reliably visible.

Note that in the above description, the example in which the α-blending ratio is spatially changed has been described, but the visible-light superimposition rate may be uniform over the entire screen. Unless an image particularly obstructs observation, as in the image 500 and image 502 illustrated in FIG. 8, there is no particular problem even if the visible-light superimposition rate is uniform over the entire screen.

Figure 7:
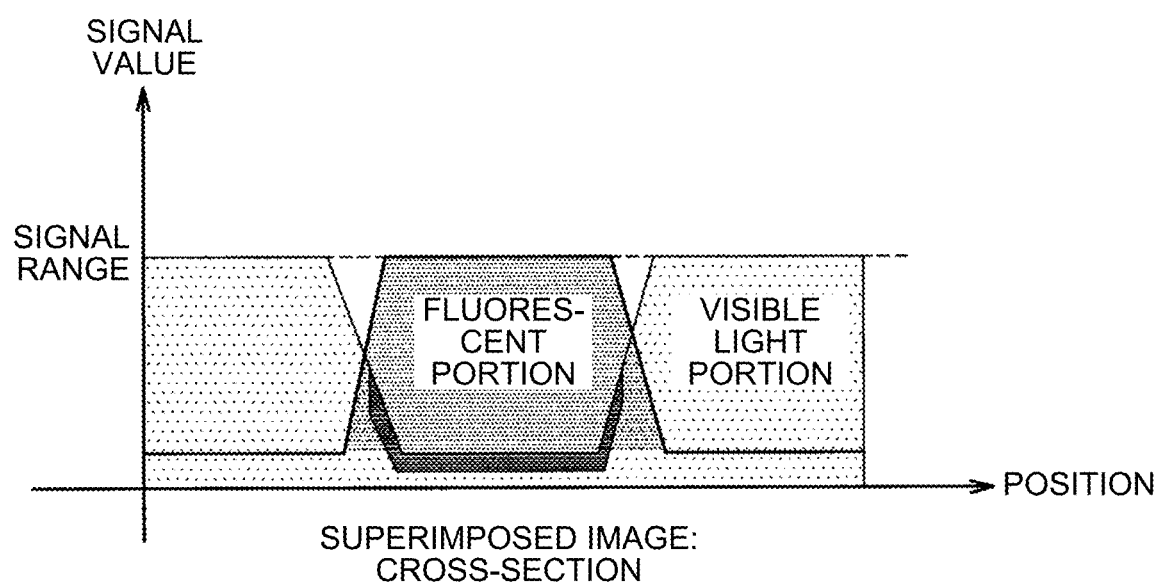
FIG. 7 is a characteristic diagram illustrating a characteristic of a signal range as a luminance component.

FIG. 7 is a characteristic diagram illustrating a characteristic of a signal range as a luminance component. As illustrated in FIG. 7, when the signal range is regarded as the luminance component, it appears that there is no difference in luminance between a fluorescent portion and a visible light portion, having a low luminance contrast. However, in the signal, the fluorescent portion actuality has a color other than that of a living body (green, cyan, etc.), and therefore, sufficient color contrast remains. Therefore, superimposition without signal saturation can be achieved while maintaining visibility.

Figure 9:
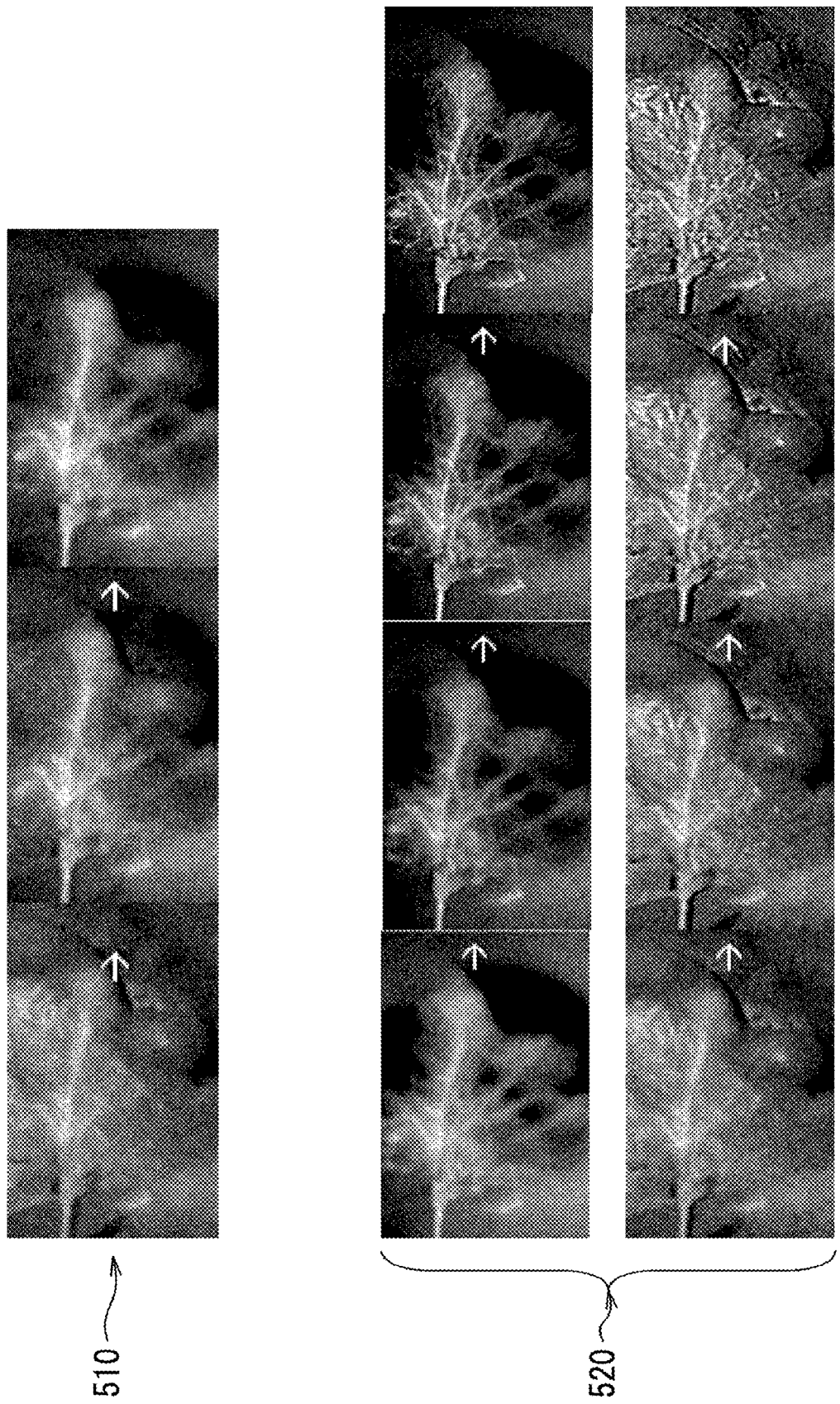
FIG. 9 is a schematic diagram illustrating an example of an image in which the degree of superimposition of a superimposed image is adjusted and an example of an image in which the degree of structure enhancement is adjusted.

FIG. 9 is a schematic diagram illustrating an example of an image 510 in which the degree of superimposition of a superimposed image is adjusted and an example of an image 520 in which the degree of structure enhancement is adjusted. In general, it is preferable to control whether to always show a visible light image serving as a background by the user depending on type of operation or scene.

In the images 510 and 520 illustrated in FIG. 9, a portion that looks white near the center is obtained from a fluorescence image, and a circumferential portion that looks black is obtained from a visible light image. In the image 510, the image has a lower visible-light superimposition rate toward the right side of the image. As shown in the image 510, the lower the visible-light superimposition rate, the darker a visible light region in the background, and a fluorescent portion can be readily observed. Thus, the fluorescent portion can be observed even when the luminance of the fluorescent portion decays, and even with the decayed fluorescence emission, the observation time can be extended.

Furthermore, in the image 520 illustrated in FIG. 9, the visible light image and the fluorescence image each have a higher degree of structure enhancement (frequency of a pixel value) toward the right side of the image. Since the higher the frequency of a pixel value the finer the image, even if the luminance of fluorescence decays, the fluorescent portion of the fluorescence image can be observed, and the observation time can be extended.

As illustrated in FIG. 9, the parameters are prepared to adjust the visible-light superimposition rate and adjust the brightness, saturation, and structure enhancement of the fluorescence image and the visible light image.

4. Configuration of Observation Time Estimation Unit

Figure 10:
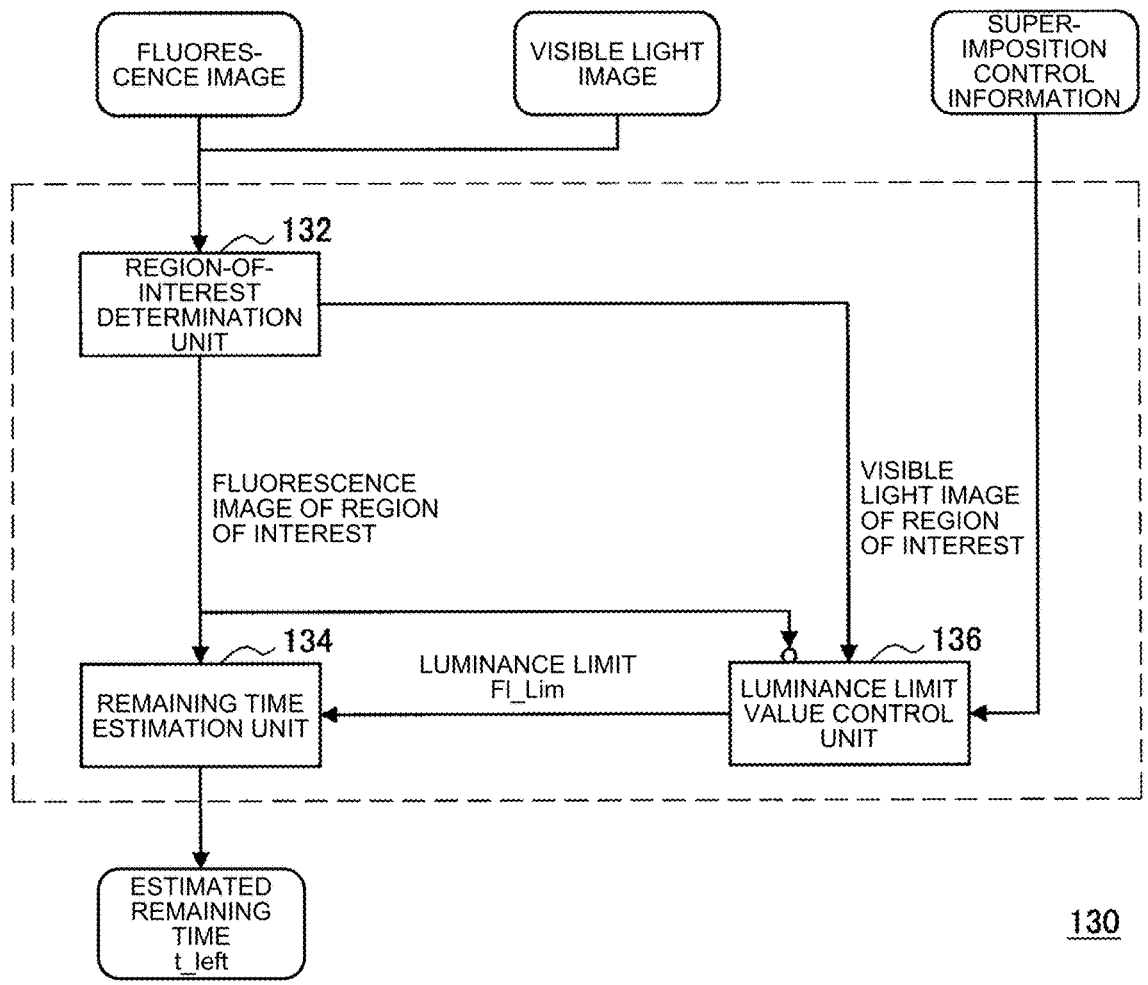
FIG. 10 is a schematic diagram illustrating a configuration of an observation time estimation unit.

FIG. 10 is a schematic diagram illustrating a configuration of the observation time estimation unit 130. The observation time estimation unit 130 includes a region-of-interest determination unit 132, a remaining time estimation unit 134, and a luminance limit value control unit 136.

Figure 11A:
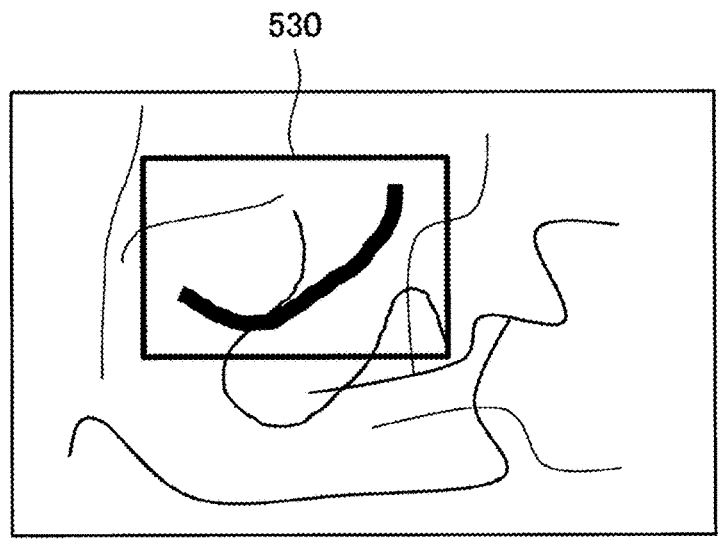
FIG. 11A is a schematic diagram illustrating an example in which a region having a peak fluorescence luminance is defined as a region of interest.
Figure 11B:
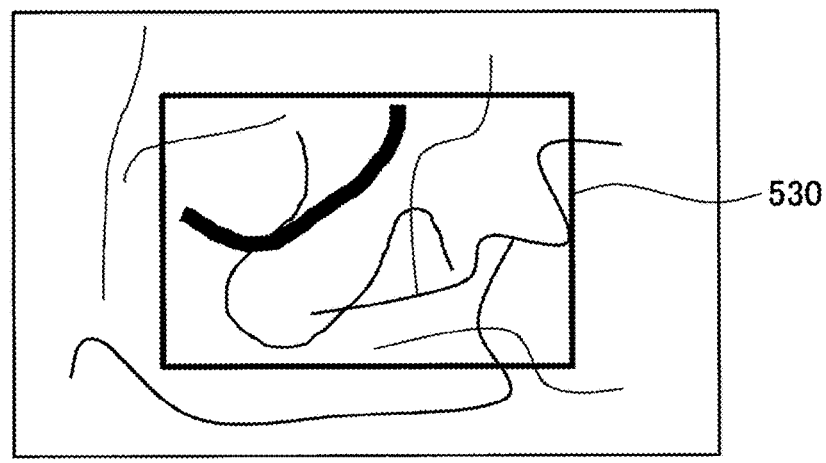
FIG. 11B is a schematic diagram illustrating an example in which a predetermined area near the center is set as a region of interest.
Figure 11C:
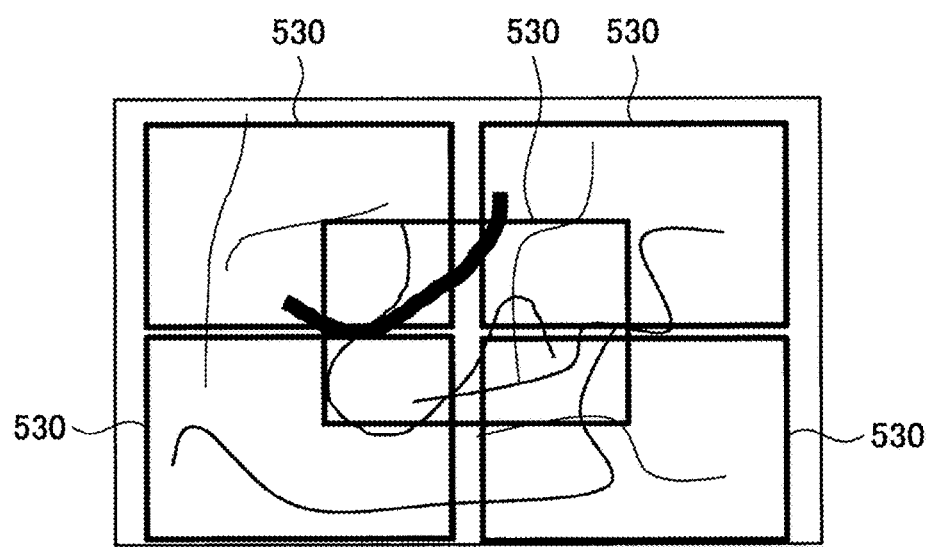
FIG. 11C is a schematic diagram illustrating an example in which a user specifies a region of interest.

The region-of-interest determination unit 132 determines an observation target area in a scene. FIGS. 11A to 11C are schematic diagrams each illustrating a method of determining a region of interest 530 from a screen obtained by imaging, by the region-of-interest determination unit 132. FIGS. 11A to 11C each illustrate a display screen of the display device 1200.

FIG. 11A is a schematic diagram illustrating an example in which when a desired area having a size corresponding to that of the region of interest 530 is set in the screen, a region having a highest luminance (region having an average luminance peak in the area) is determined as the region of interest 530. Furthermore, in the example illustrated in FIG. 11A, after a desired time period of observation, an appropriate area around a region having a fluorescence luminance peak can be automatically determined as the region of interest 530.

FIG. 11B is a schematic diagram illustrating an example in which a predetermined area near the center is set as an appropriate region of interest 530. FIG. 11C is a schematic diagram illustrating an example in which the user specifies the region of interest 530. In the example illustrated in FIG. 11C, the user selects the region of interest 530 from a plurality of predetermined areas (upper right, lower right, center, upper left, lower left, etc.). For example, in addition to a method of selection by voice, the user can operate a touch panel or the like provided in the imaging device 1100, a camera control unit, or the like, input operation information to the operation input unit 170, and select the region of interest 530.

Figure 12:
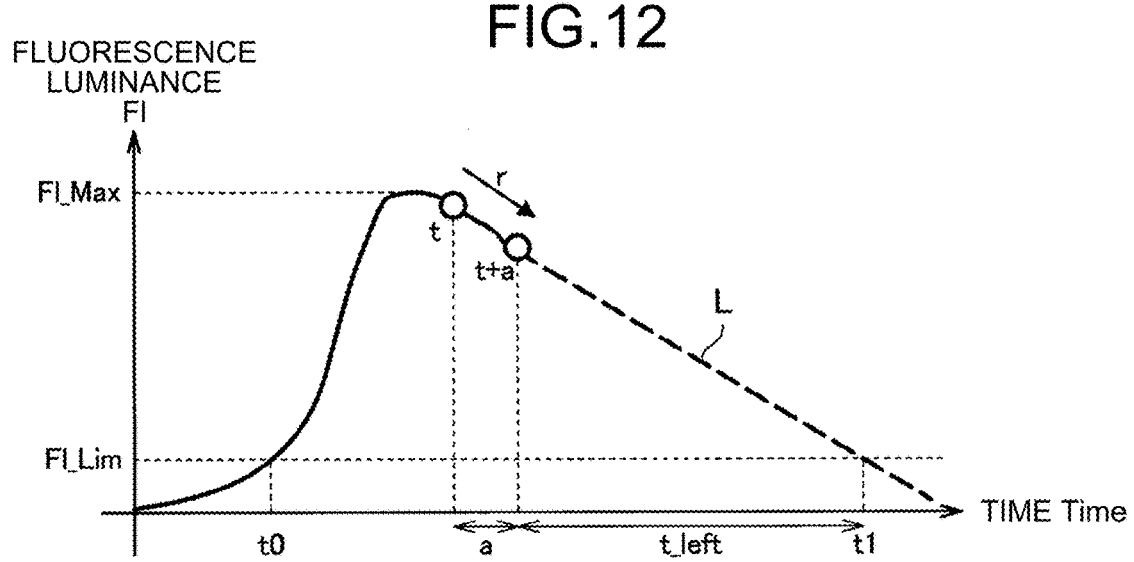
FIG. 12 is a characteristic diagram illustrating a relationship between average luminance of a fluorescent portion (vertical axis) and time (horizontal axis) in a region of interest.

The remaining time estimation unit 134 estimates a remaining time in which fluorescence is visible in the region of interest 530 determined by the region-of-interest determination unit 132. As a specific method of estimating a remaining time in the remaining time estimation unit 134, a method of obtaining the remaining time from a decay rate in fluorescence time will be described below. FIG. 12 is a characteristic diagram illustrating a relationship between average luminance of a fluorescent portion (vertical axis) and time (horizontal axis) in a region of interest 530. As illustrated in FIG. 12, in the relationship between average luminance of fluorescent portions (vertical axis) and time (horizontal axis), a characteristic curve having an emission peak is obtained. For example, in observation of a liver by injecting ICG into a vein, until the ICG reaches the liver after the ICG is injected into a vein of an arm, fluorescence luminance in the region of interest 530 (liver) increases and then decays after reaching a peak. Here, a gradient r of decay in fluorescence luminance can be determined from the time t slightly after peak luminance and luminance at the time t+a, after a time a has elapsed from the time t.

When the luminance of the fluorescent portion decays, it becomes difficult to observe fluorescence. In FIG. 12, luminance limit of fluorescent observation is Fl_Lim. A value of Fl_Lim is set by the luminance limit value control unit 136. In FIG. 12, on the basis of the gradient r and luminance information at time t+a, a broken line L is drawn following the gradient, obtaining the time t1 at which the broken line L intersects the luminance limit Fl_Lim. Thus the remaining time to the luminance limit Fl_Lim from the time t+a can be estimated. An estimated remaining time t_left can be calculated according to the following formula.

$$t\_left = t1 - (t+a)$$

For estimation of the remaining time, it is also possible to perform approximation using various fitting curves instead of estimation using a straight line with the gradient r. For example, three or more combinations of values of time and luminance after the peak luminance can be used to perform approximation by using polynomial approximation, a Gaussian function, a Lorentz function, and the like. It is also possible to calculate the time at which these approximation functions show the luminance limit Fl_Lim to obtain the estimated remaining time as in the case of using the broken line L.

Figure 13:
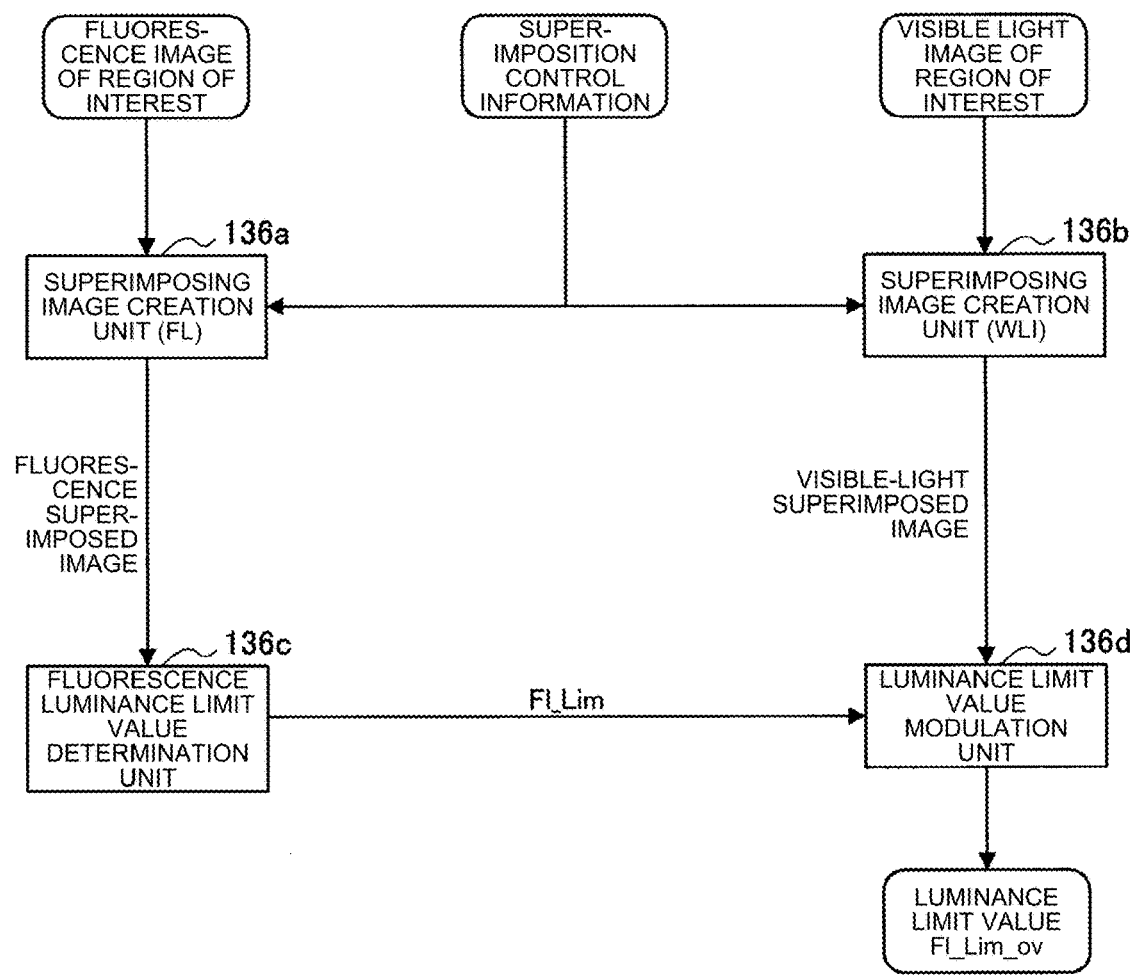
FIG. 13 is a schematic diagram illustrating a configuration of a luminance limit control unit.

Furthermore, the luminance limit value control unit 136 controls the luminance limit Fl_Lim on the basis of various information about a fluorescence image and a visible light image which are superimposed each other in the region of interest 530. FIG. 13 is a schematic diagram illustrating a configuration of the luminance limit value control unit 136. As illustrated in FIG. 13, the luminance limit value control unit 136 includes a superimposing image creation unit (FL) 136a that creates a superimposing image of a fluorescence image, a superimposing image creation unit (WLI) 136b that creates a superimposing image of a visible light image, a fluorescence luminance limit value determination unit 136c that determines a luminance limit value of fluorescence only, and a luminance limit value modulation unit 136d.

Figure 14A:
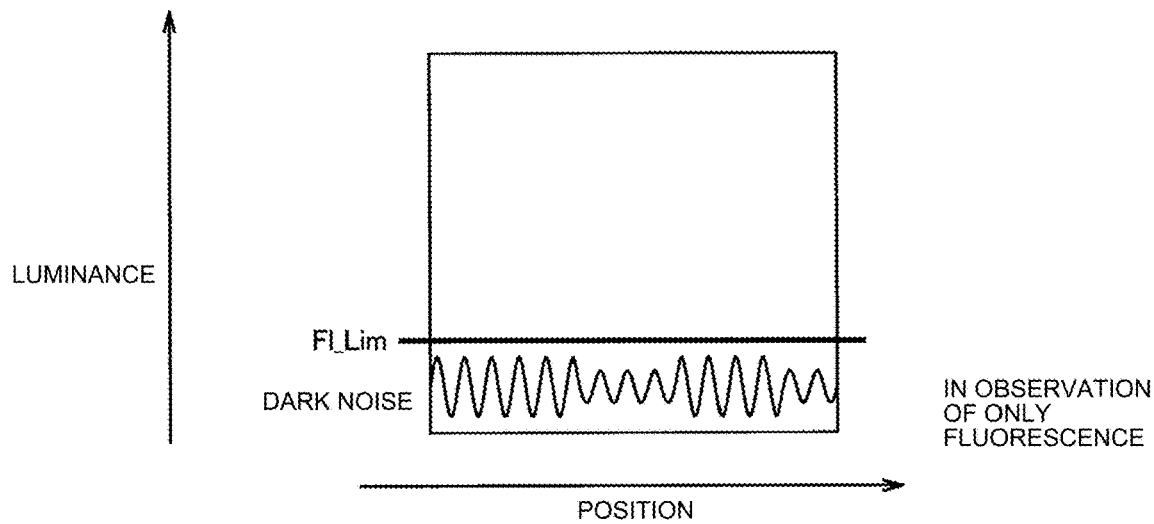
FIG. 14A is a schematic diagram illustrating a method of determining a luminance limit value Fl_Lim.
Figure 14B:
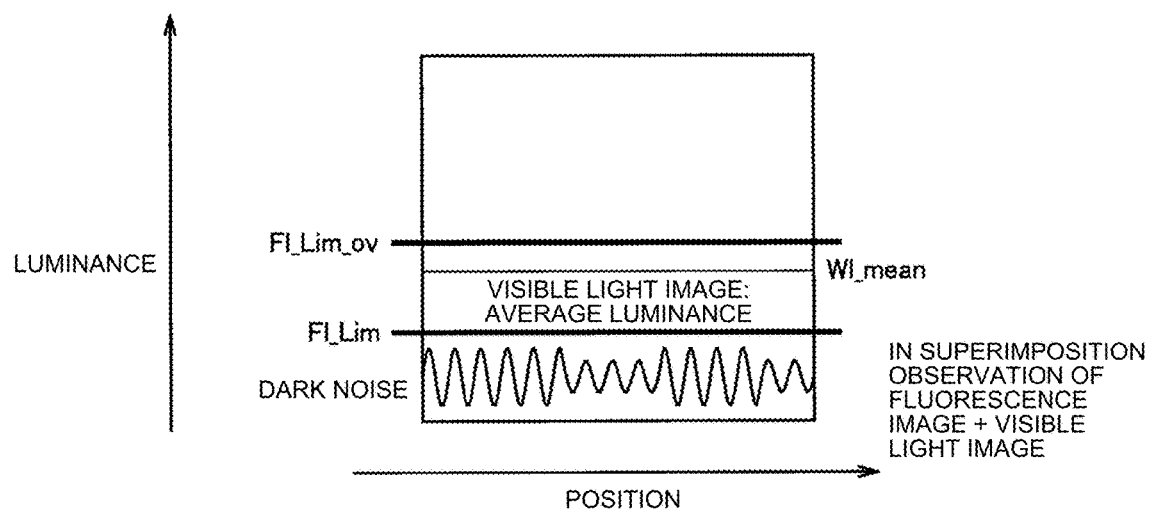
FIG. 14B is a schematic diagram illustrating a method of determining a luminance limit value Fl_Lim.

FIGS. 14A and 14B are schematic diagrams each illustrating a method of determining a luminance limit value Fl_Lim. FIG. 14A illustrates a method of determining the luminance limit value Fl_Lim in a case where only a fluorescence image is observed. FIG. 14B illustrates a method of determining the luminance limit value Fl_Lim in a case where a superimposed image of a fluorescence image and a visible light image is observed.

As illustrated in FIG. 14A, in observation of only the fluorescence image, the luminance limit value Fl_Lim is set as a luminance value at which the fluorescence image is not buried in dark noise, by using a fluorescence image of the region of interest 530. A dark area in the fluorescence image may be detected under a condition that the dark area has a value equal to or less than a certain luminance value, and the standard deviation of an image of the dark area may be defined as a noise amount. By setting the luminance limit value Fl_Lim to a value larger than the noise amount, the fluorescence image is not buried in the dark noise, and the fluorescence image is reliably observable.

When observing the superimposed image, processing of FIG. 14B is performed in addition to the processing of FIG. 14A. Before performance of the processing of FIG. 14B, the superimposing image creation unit (FL) 136a for fluorescence image processes the fluorescence image of the region of interest 530 at an α-blending ratio and generates a fluorescence superimposed image of the region of interest 530. The superimposing image creation unit (WLI) 136b for visible light image processes a visible light image of the region of interest 530 at an α-blending ratio to generate a visible-light superimposed image of the region of interest 530.

Then, by the method illustrated in FIG. 14A, the fluorescence luminance limit value determination unit 136c sets a luminance value at which the fluorescence image is not buried in dark noise as a luminance limit value Fl_Lim, by using the fluorescence superimposed image.

The luminance limit value modulation unit 136d receives input of the luminance limit value Fl_Lim set by the fluorescence luminance limit value determination unit 136c and the visible-light superimposed image. The luminance limit value modulation unit 136d changes the luminance limit value Fl_Lim and outputs a luminance limit value Fl_Lim_ov.

As an example, as illustrated in FIG. 14B, it is assumed that the visible-light superimposed image has an average luminance Wl_mean which is larger than the luminance limit value Fl_Lim of the fluorescence superimposed image. In this case, if the luminance limit value Fl_Lim is not changed to a value Fl_Lim_ov at least larger than the average luminance Wl_mean, the fluorescence superimposed image is buried in the visible-light superimposed image and becomes invisible. Therefore, the luminance limit value Fl_Lim is controlled according to a state of the visible-light superimposed image. In a case of the example illustrated in FIG. 14B, by changing the luminance limit value Fl_Lim to Fl_Lim_ov, a superimposing image FL of a fluorescence image is reliably visible.

The control of the luminance limit value as described above can be achieved by calculating Fl_Lim_ov according to the following formula.

$$Fl\_Lim\_ov = FL\_Lim + a*(WL\_mean - FL\_Lim) \text{ (However, } a > 1.0)$$

Furthermore, when Wl_mean≤Fl_lim, the luminance limit value is controlled to the luminance limit value Fl_Lim set by the fluorescence luminance limit value determination unit 136*c*.

In the above formula, it is possible to appropriately set a coefficient a to a value larger than 1.0 to automatically control the luminance limit value Fl_Lim. The features of a visible light image that affects the luminance limit value Fl_Lim includes luminance (average value, maximum value, mode, etc.), saturation (average value, mode, etc.), bandwidth (e.g., covering higher frequency ranges than a certain frequency range), and the like.

For example, when the luminance (average value, maximum value, or mode, etc.) of the visible light image is larger, the value of the coefficient a is increased to increase the luminance limit value Fl_Lim. Furthermore, when the saturation (average value, or mode, etc.) of the visible light image is larger, the value of the coefficient a is increased to increase the luminance limit value Fl_Lim. The greater the luminance or saturation of a visible light image, the more difficult it is for the user to see a fluorescent portion. Therefore, when the luminance or saturation of the visible light image is larger, the luminance limit value Fl_Lim is increased, and the estimated remaining time t_left can be calculated more accurately.

Furthermore, when the visible light image has a bandwidth covering higher frequency ranges than a certain frequency range, the value of the coefficient a is increased to increase the luminance limit value Fl_Lim. When the bandwidth of the visible light image covers a higher frequency range, it is difficult for the user to see the fluorescent portion. Therefore, when the bandwidth of the visible light image covers a higher frequency range, the luminance limit value Fl_Lim is increased, and the estimated remaining time t_left can be calculated accurately.

5. Configuration of Display Processing Unit

Figure 15A:
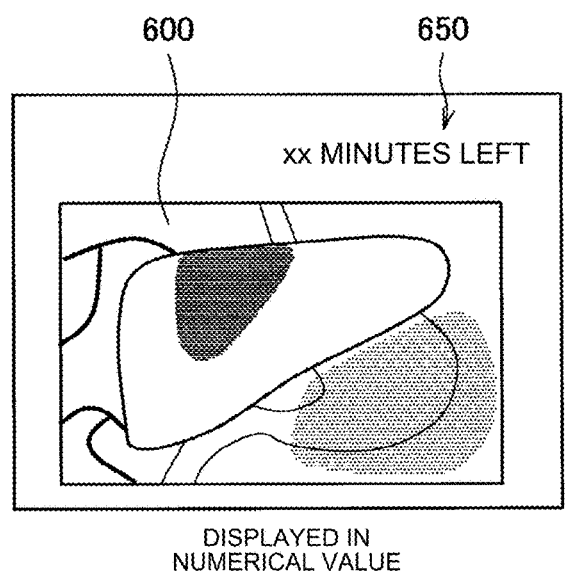
FIG. 15A is a schematic diagram illustrating an image displayed on a display device according to a result of processing performed by a display processing unit.
Figure 15B:
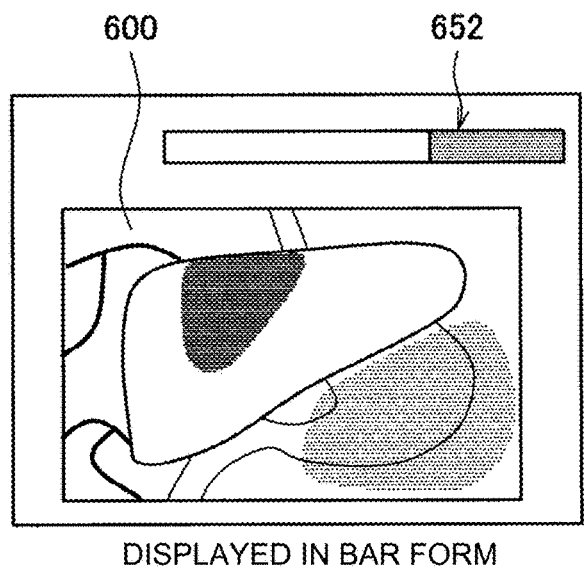
FIG. 15B is a schematic diagram illustrating an image displayed on a display device according to a result of processing performed by a display processing unit.

The display processing unit 140 performs processing for appropriately presenting a superimposed image and an estimated remaining time to the user from the display device 1200. FIGS. 15A to 15D are schematic diagrams each illustrating an image displayed on the display device 1200 according to a result of processing performed by the display processing unit 140. FIG. 15A illustrates an example in which an estimated remaining time is displayed in numerical value 650 on the same screen as a superimposed image 600. FIG. 15B illustrates an example in which an estimated remaining time is displayed in graphic form (bar form, etc.) 652 on the same screen as the superimposed image 600.

Figure 15C:
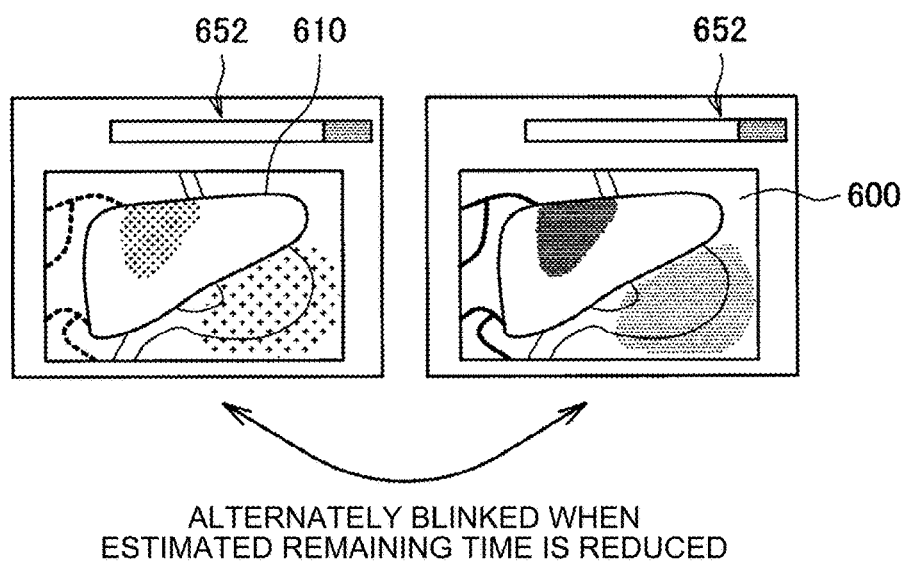
FIG. 15C is a schematic diagram illustrating an image displayed on a display device according to a result of processing performed by a display processing unit.
Figure 15D:
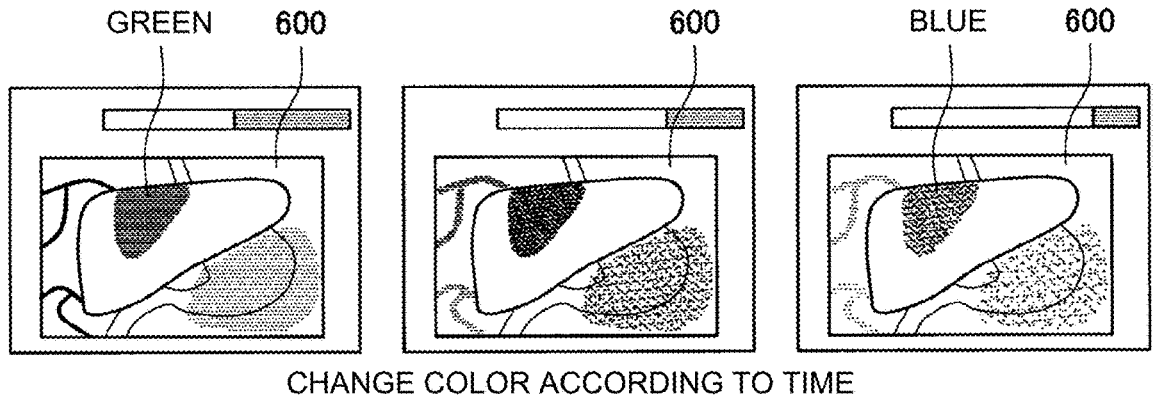
FIG. 15D is a schematic diagram illustrating an image displayed on a display device according to a result of processing performed by a display processing unit.

Furthermore, FIG. 15C illustrates an example in which when the estimated remaining time decreases, the superimposed image 600 and a fluorescence image 610 (or visible light image) are caused to blink alternately, changing blinking speed according to the estimated remaining time (raising blinking speed). FIG. 15D illustrates an example in which when the estimated remaining time decreases, the color of a fluorescent portion in the superimposed image 600 is caused to change according to the estimated remaining time to notify that the remaining time is reduced. FIG. 15D illustrates a case in which the color of the fluorescent portion is caused to change from green to blue (cyan) according to the decrease in the estimated remaining time.

In addition to the methods illustrated in FIGS. 15A to 15C, for example, when the estimated remaining time decreases, alert sound may be made instead of displaying the estimated remaining time on the screen. The estimated remaining time may be presented by one of the above-described methods alone or may be presented by using some of the methods.

6. About Extension of Remaining Observation Time

Figure 16:
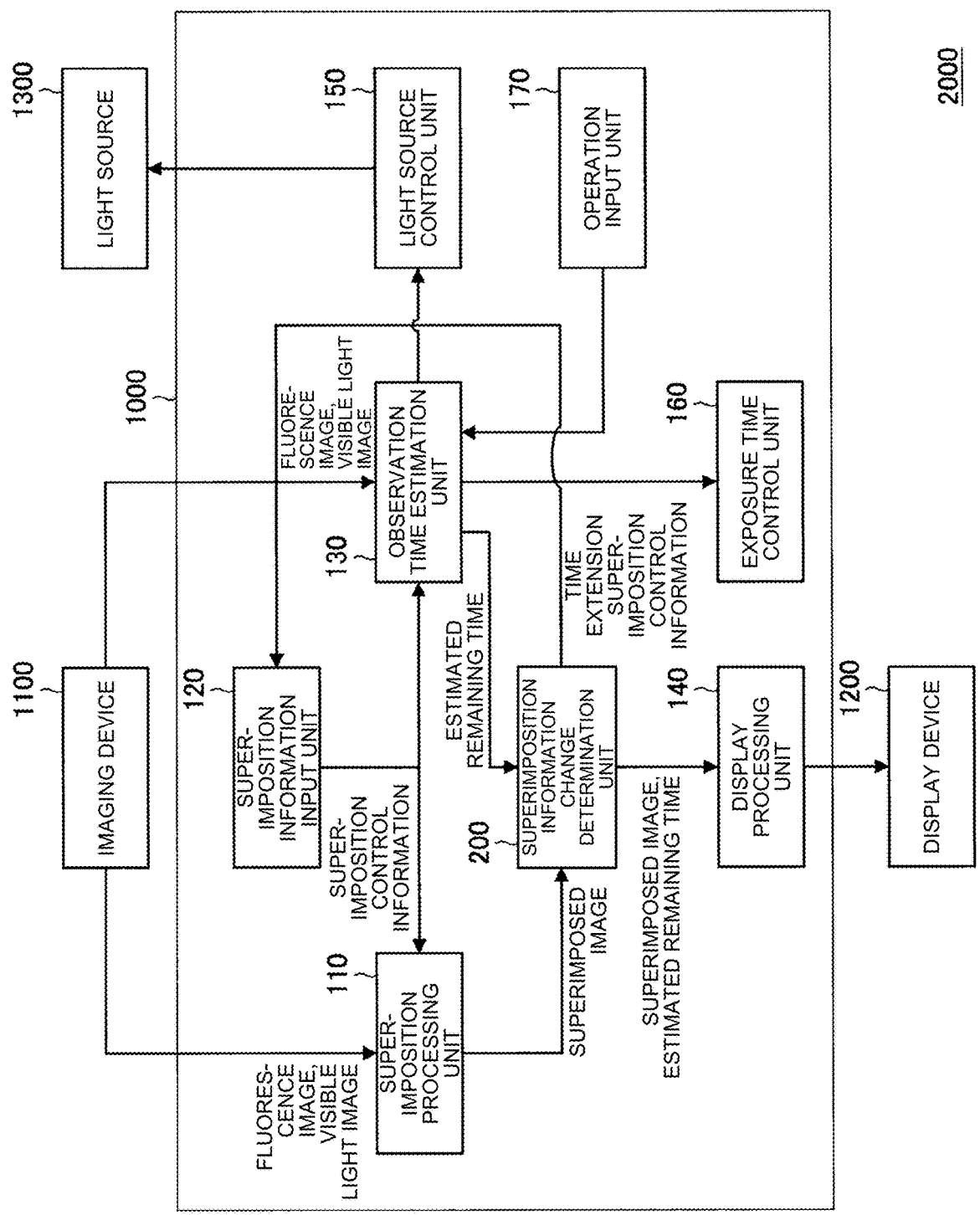
FIG. 16 is a schematic diagram illustrating an example in which a superimposition information change determination unit is added to the configuration of FIG. 1.

FIG. 16 is a schematic diagram illustrating an example in which a superimposition information change determination unit 200 is added to the configuration of FIG. 1. Provision of the superimposition information change determination unit 200 enables superimposition control information to be automatically or manually changed when a fluorescence image becomes dark, extending the observation time.

The superimposition information change determination unit 200 determines whether to change the superimposition control information on the basis of an estimated remaining time t_left.

Figure 17:
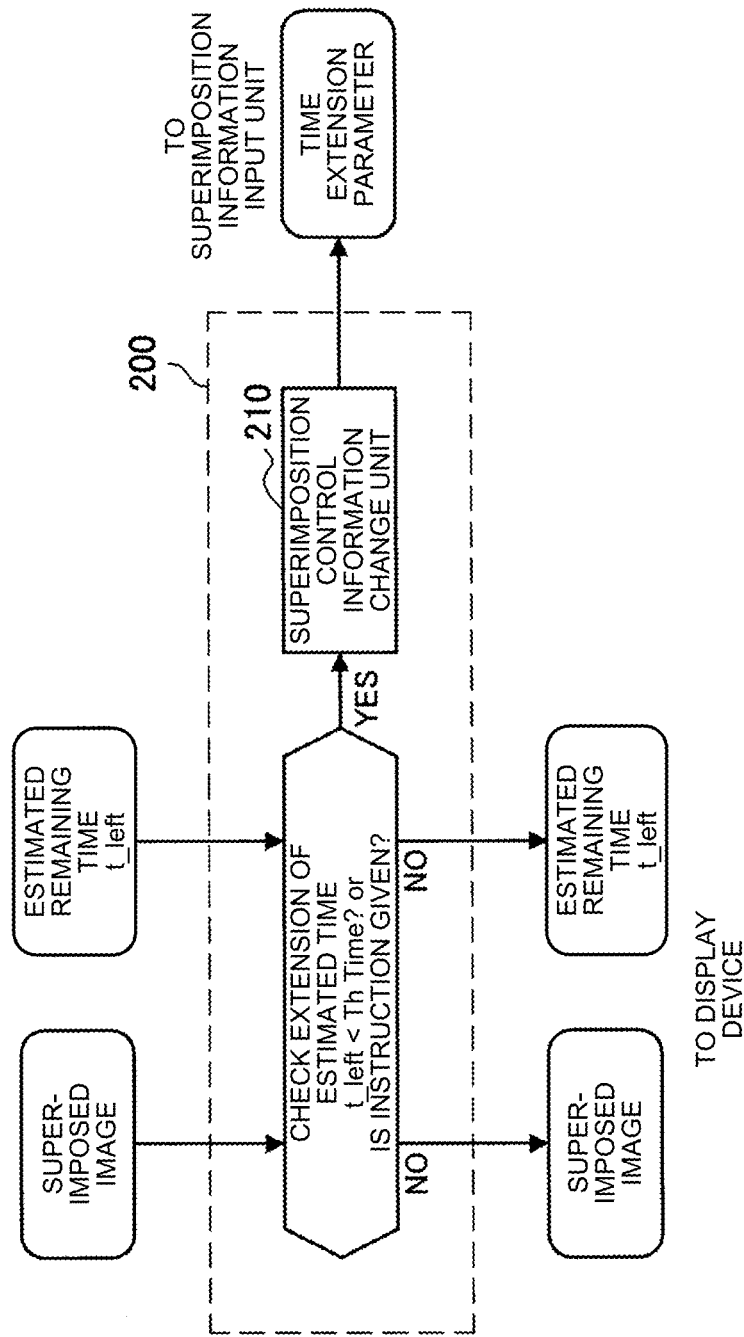
FIG. 17 is a schematic diagram illustrating a configuration of the superimposition information change determination unit.

FIG. 17 is a schematic diagram illustrating a configuration of the superimposition information change determination unit 200. The superimposition information change determination unit 200 determines whether to change the superimposition control information according to whether the estimated remaining time t_left is shorter than an observation limit time ThTime. Furthermore, the superimposition information change determination unit 200 determines whether to change the superimposition control information on the basis of instruction, such as voice, line of sight, or gesture, of the user.

The superimposition information change determination unit 200 includes a superimposition control information change unit 210. When the change of the superimposition control information is determined, the superimposition control information change unit 210 changes the superimposition control information and outputs the changed superimposition control information prompting extension of the observation time. The changed superimposition control information is sent to the superimposition information input unit 120.

On the other hand, when the superimposition information change determination unit 200 determines that the superimposition control information is not to be changed, a superimposed image and the estimated remaining time are sent to the display processing unit 140 and presented from the display device 1200 to the user.

Examples of the change of the superimposition control information by the superimposition information change determination unit 200 include reducing the superimposition rate of a visible light image, reducing the saturation of a visible light image, reducing the bandwidth of a visible light image (blurring), and the like.

In a case of reducing the superimposition rate of the visible light image, the superimposition control information indicating the reduction is sent to the superimposition information input unit 120 and further sent to the superimposition processing unit 110. Thereby, in the superimposition processing unit 110, superimposition is performed with a reduced superimposition rate of the visible light image. Lowering the superimposition rate of the visible light image reduces the average luminance Wl_mean illustrated in FIG. 14B, and the fluorescence image becomes readily visible (including display of single fluorescence image). Accordingly, as in the example of the image 510 illustrated in FIG. 9, the lower the visible-light superimposition rate, the darker a visible light region in the background, and a fluorescent portion can be readily observed. Therefore, even if fluorescence emission decays, the observation time can be extended.

In a case of reducing the saturation of the visible light image, the superimposition control information indicating the reduction is sent to the superimposition information input unit 120 and further sent to the superimposition processing unit 110. The visible light image processing unit 116 of the superimposition processing unit 110 performs processing of reducing the saturation of the visible light image on the basis of the superimposition control information. Lowering the saturation of the visible light image reduces the average luminance Wl_mean illustrated in FIG. 14B, and the fluorescence image becomes readily visible.

Furthermore, in a case of reducing the bandwidth of the visible light image (blurring a visible light image), the superimposition control information indicating the reduction is sent to the superimposition information input unit 120 and further sent to the superimposition processing unit 110. The visible light image processing unit 116 of the superimposition processing unit 110 performs processing of reducing the bandwidth of the visible light image on the basis of the superimposition control information. Reducing the bandwidth (blurring) of the visible light image reduces texture in a superimposed image and emphasizes the structure of a fluorescence image, and the fluorescence image becomes readily visible. Thus, as in the example of the image 520 illustrated in FIG. 9, the higher the frequency of a pixel value is the finer the image is, and even if the luminance of fluorescence decays, the fluorescent portion of the fluorescence image can be observed, and thus the observation time can be extended.

Furthermore, for example, changing the superimposition control information by the superimposition information change determination unit 200 can include changing the fluorescence image.

In a case of increasing a luminance gain of the fluorescence image, the superimposition control information indicating the increase is sent to the superimposition information input unit 120 and further sent to the superimposition processing unit 110. The fluorescence image processing unit 118 of the superimposition processing unit 110 performs processing of reducing the bandwidth of the fluorescence image on the basis of the superimposition control information. Increasing the luminance gain of the fluorescence image increases fluorescence luminance Fl, and the fluorescence image becomes readily visible.

Furthermore, in a case of increasing the saturation of a fluorescence image, the superimposition control information indicating the increase is sent to the superimposition information input unit 120 and further sent to the superimposition processing unit 110. The fluorescence image processing unit 118 of the superimposition processing unit 110 performs processing of reducing the saturation of the fluorescence image on the basis of the superimposition control information. The saturation (green in a case of using ICG) of the fluorescence image is increased and the fluorescence image becomes readily visible.

In a case of increasing the bandwidth of the fluorescence image, the superimposition control information indicating the increase is sent to the superimposition information input unit 120 and further sent to the superimposition processing unit 110. The fluorescence image processing unit 118 of the superimposition processing unit 110 performs processing of increasing the bandwidth of the fluorescence image on the basis of the superimposition control information. Increasing the bandwidth of the fluorescence image emphasizes the structure of the fluorescence image, and the fluorescence image becomes readily visible.

Note that control of the luminance, saturation, and bandwidth of the visible light image may be performed by the superimposing image creation unit (WLI) 136b on the basis of the superimposition control information. Similarly, control of the luminance, saturation, and bandwidth of the fluorescence image may be performed by the superimposing image creation unit (FL) 136a. In this configuration, the superimposition processing unit 110 receives the visible light image from the superimposing image creation unit (WLI) 136b, receives the fluorescence image from the superimposing image creation unit (FL) 136a, and performs superimposition processing.

Time extension can also be performed by increasing the brightness of light emitted from the light source 1300. The illuminance of the light source 1300 is controlled by the light source control unit 150. The light source control unit 150 receives input of an estimated remaining time t_left estimated by the remaining time estimation unit 134 of the observation time estimation unit 130. When the estimated remaining time t_left becomes shorter than an observation limit time ThTime, the light source control unit 150 sends control information to the light source 1300 and performs control to increase the brightness of light emitted from the light source 1300. Accordingly, a fluorescent portion of a superimposed image emits brighter light, and the fluorescence image becomes readily visible.

Furthermore, extension can also be performed by extending an exposure time of the imaging device 1100. The exposure time is controlled by the exposure time control unit 160. The exposure time control unit 160 receives input of an estimated remaining time t_left estimated by the remaining time estimation unit 134 of the observation time estimation unit 130. When the estimated remaining time t_left becomes shorter than an observation limit time ThTime, the exposure time control unit 160 sends control information to the imaging device 1100 and performs control to increase the exposure time upon exposure of a fluorescence image. For example, the imaging device 1100 having received the control information performs processing of increasing the exposure time per frame by reducing the number of frames per unit time. Accordingly, a fluorescent portion of a superimposed image becomes brighter, and the fluorescence image becomes readily visible.

The time extension by controlling the exposure time is suitable particularly for less movement of an object. For example, when capturing a brain image as an object in brain surgery or the like, the object has less movement, and it is possible to suppress a decrease in image quality due to an increased exposure time and a reduced number of frames.

As described above, according to the present embodiment, time information for fluorescence image observation is presented, and the doctor can perform fluorescent observation without stress. Therefore, it is possible to reliably concentrate on observation of an important scene for which fluorescent observation is desired during surgery, and prevention of surgical accidents can be promoted.

Furthermore, when the fluorescence image is getting dark, observation time extension processing can be performed according to remaining observation time and necessity. Therefore, it is possible to suppress excessive administration of additional agents to reduce invasiveness.

The preferred embodiments of the present disclosure have been described above in detail with reference to the accompanying drawings, but the technical scope of the present disclosure is not limited to such examples. A person skilled in the art may obviously find various alternations and modifications within the technical ideas as set forth in the scope of the appended claims, and it should be understood that they will naturally come under the technical scope of the present invention.

In addition, the effects described herein are merely illustrative and demonstrative and are not limitative. In other words, the technology according to the present disclosure can exhibit, along with or instead of the effects, other effects apparent to those skilled in the art from the description herein.

Additionally, the technical scope of the present disclosure may include the following structure.

(1)

An information processing device comprising a remaining time estimation unit that estimates, on the basis of a luminance limit value for observation of a fluorescence image and a change in luminance of a fluorescence image, a remaining time until the luminance of the fluorescence image reaches the luminance limit value.

(2)

The information processing device according to (1), wherein the remaining time estimation unit estimates the remaining time, on the basis of a reduction process of reduction in the luminance of the fluorescence image having reached a peak due to administration of a fluorescent agent to an object.

(3)

The information processing device according to (2), wherein the remaining time estimation unit estimates the remaining time on the basis of a reduction rate of the luminance of the fluorescence image in the reduction process.

(4)

The information processing device according to (2), wherein the remaining time estimation unit estimates the remaining time by applying the luminance of the fluorescence image in the reduction process to a predetermined function.

(5)

The information processing device according to any one of (1) to (4), further comprising a luminance limit value control unit that controls the luminance limit value, wherein the luminance limit value control unit controls the luminance limit value on the basis of a noise of the fluorescence image.

(6)

The information processing device according to any one of (1) to (5), further comprising a superimposition processing unit that superimposes the fluorescence image and a visible light image on each other.

(7)

The information processing device according to (5), wherein the luminance limit value control unit controls the luminance limit value on the basis of a luminance of a visible light image superimposed on the fluorescence image.

(8)

The information processing device according to (5), wherein the luminance limit value control unit controls the luminance limit value on the basis of a saturation of a visible light image superimposed on the fluorescence image.

(9)

The information processing device according to (5), wherein the luminance limit value control unit controls the luminance limit value on the basis of a frequency characteristic of a visible light image superimposed on the fluorescence image.

(10)

The information processing device according to any one of (1) to (9), wherein the remaining time estimation unit estimates the remaining time on the basis of a change in the luminance of the fluorescence image in a region of interest.

(11)

The information processing device according to (10), wherein the region of interest includes an area where the luminance of the fluorescence image has a spatial peak on a screen.

(12)

The information processing device according to (10), wherein the region of interest is a central area of the fluorescence image or an area set on the basis of a user's operation input.

(13)

The information processing device according to any one of (1) to (12), further comprising a display processing unit that performs processing of causing a display device to display the remaining time.

(14)

The information processing device according to (13), wherein the display processing unit causes the remaining time to be displayed in numerical value or in bar form.

(15)

The information processing device according to (13), wherein the display processing unit causes at least the fluorescence image to be blinked according to the remaining time or causes a color of the fluorescence image to be changed according to the remaining time.

(16)

The information processing device according to (6), wherein the superimposition processing unit reduces a superimposition rate of the visible light image to the fluorescence image when the remaining time is smaller than a predetermined value.

(17)

The information processing device according to (6), further comprising an image processing unit that performs image processing on the visible light image or the fluorescence image when the remaining time is smaller than a predetermined value.

(18)

The information processing device according to (17), wherein the image processing unit changes a luminance, saturation, or a bandwidth of the visible light image or the fluorescence image.

(19)

An information processing method comprising estimating, on the basis of a luminance limit value for observation of a fluorescence image and a change in luminance of a fluorescence image, a remaining time until the luminance of the fluorescence image reaches the luminance limit value.

(20)

A fluorescence image capturing system comprising:

an imaging device that captures a fluorescence image;

a light source that emits light to an object imaged by the imaging device; and an information processing device including a remaining time estimation unit that estimates, on the basis of a luminance limit value for observation of a fluorescence image and a change in luminance of a fluorescence image, a remaining time until the luminance of the fluorescence image reaches the luminance limit value.

REFERENCE SIGNS LIST

110 SUPERIMPOSITION PROCESSING UNIT
116 VISIBLE LIGHT IMAGE PROCESSING UNIT
118 FLUORESCENCE IMAGE PROCESSING UNIT

134 REMAINING TIME ESTIMATION UNIT
136 LUMINANCE LIMIT VALUE CONTROL UNIT
140 DISPLAY PROCESSING UNIT
1000 IMAGE PROCESSING DEVICE
1100 IMAGING DEVICE
1200 DISPLAY DEVICE
1300 LIGHT SOURCE

The invention claimed is:

1. An information processing device comprising circuitry configured to:
   estimate, on a basis of a current luminance level of a fluorescence image, a luminance limit value for observation of the fluorescence image, and a rate of decay in luminance of the fluorescence image, a remaining time until the luminance of the fluorescence image reaches the luminance limit value;
   superimpose the fluorescence image and a visible light image on each other; and
   reduce a superimposition rate of the visible light image to the fluorescence image when the remaining time is smaller than a predetermined value,
   wherein the luminance limit value corresponds to a minimum level at which the fluorescence image remains observable over noise in the fluorescence image.

2. The information processing device according to claim 1, wherein the circuitry is further configured to estimate the remaining time, on the basis of a reduction process of reduction in the luminance of the fluorescence image having reached a peak due to administration of a fluorescent agent to an object.

3. The information processing device according to claim 2, wherein the circuitry is further configured to estimate the remaining time on the basis of a reduction rate of the luminance of the fluorescence image in the reduction process.

4. The information processing device according to claim 2, wherein the circuitry is further configured to estimate the remaining time by applying the luminance of the fluorescence image in the reduction process to a predetermined function.

5. The information processing device according to claim 1, wherein the circuitry is further configured to control the luminance limit value on the basis of a noise of the fluorescence image.

6. The information processing device according to claim 5, wherein the wherein the circuitry is further configured to control the luminance limit value on the basis of a luminance of a visible light image superimposed on the fluorescence image.

7. The information processing device according to claim 5, wherein the wherein the circuitry is further configured to control the luminance limit value on the basis of a saturation of a visible light image superimposed on the fluorescence image.

8. The information processing device according to claim 5, wherein the wherein the circuitry is further configured to control the luminance limit value on the basis of a frequency characteristic of a visible light image superimposed on the fluorescence image.

9. The information processing device according to claim 1, wherein the circuitry is further configured to estimate the remaining time on the basis of the change in the luminance of the fluorescence image in a region of interest.

10. The information processing device according to claim 9, wherein the region of interest includes an area where the luminance of the fluorescence image has a spatial peak on a screen.

11. The information processing device according to claim 9, wherein the region of interest is a central area of the fluorescence image or an area set on the basis of a user's operation input.

12. The information processing device according to claim 1, wherein the circuitry is further configured to cause a display to display the remaining time.

13. The information processing device according to claim 12, wherein the circuitry is further configured to cause the remaining time to be displayed in numerical value or in bar form.

14. The information processing device according to claim 12, wherein the circuitry is further configured to cause at least the fluorescence image to be blinked according to the remaining time or cause a color of the fluorescence image to be changed according to the remaining time.

15. The information processing device according to claim 1, wherein the circuitry is further configured to perform image processing on the visible light image or the fluorescence image when the remaining time is smaller than a predetermined value.

16. The information processing device according to claim 15, wherein the circuitry is further configured to change a luminance, saturation, or a bandwidth of the visible light image or the fluorescence image.

17. An information processing method comprising:
   estimating, on the basis of a current luminance level of a fluorescence image, a luminance limit value for observation of the fluorescence image and a rate of decay in luminance of a fluorescence image, a remaining time until the luminance of the fluorescence image reaches the luminance limit value;
   superimpose the fluorescence image and a visible light image on each other; and
   reduce a superimposition rate of the visible light image to the fluorescence image when the remaining time is smaller than a predetermined value,
   wherein the luminance limit value corresponds to a minimum level at which the fluorescence image remains observable over noise in the fluorescence image.

18. A fluorescence image capturing system comprising:
   an imager that captures a fluorescence image;
   a light source that emits light to an object imaged by the imaging device; and
   circuitry configured to:
      estimate, on the basis of a current luminance level of a fluorescence image, a luminance limit value for observation of the fluorescence image, and a rate of decay in luminance of a fluorescence image, a remaining time until the luminance of the fluorescence image reaches the luminance limit value;
      superimpose the fluorescence image and a visible light image on each other; and
      reduce a superimposition rate of the visible light image to the fluorescence image when the remaining time is smaller than a predetermined value,
   wherein the luminance limit value corresponds to a minimum level at which the fluorescence image remains observable over noise in the fluorescence image.

* * * * *